(12) United States Patent
Law et al.

(10) Patent No.: US 7,632,928 B2
(45) Date of Patent: Dec. 15, 2009

(54) METHOD AND ANTIBODIES FOR DETECTING NITROFURAN

(75) Inventors: Say-Jong Law, Westwood, MA (US);
Stanley E. Charm, Boston, MA (US);
Steven J. Saul, Arlington, MA (US)

(73) Assignee: Charm Sciences, Inc, Lawrence, MA (US)

( * ) Notice: Subject to any disclaimer, the term of this patent is extended or adjusted under 35 U.S.C. 154(b) by 191 days.

(21) Appl. No.: 11/583,236

(22) Filed: Oct. 18, 2006

(65) Prior Publication Data
US 2007/0054340 A1 Mar. 8, 2007

Related U.S. Application Data

(63) Continuation of application No. PCT/US2006/032443, filed on Aug. 21, 2006, and a continuation-in-part of application No. PCT/US2005/012898, filed on Apr. 15, 2005.

(60) Provisional application No. 60/710,026, filed on Aug. 19, 2005, provisional application No. 60/563,340, filed on Apr. 19, 2004, provisional application No. 60/563,779, filed on Apr. 20, 2004, provisional application No. 60/565,364, filed on Apr. 26, 2004.

(51) Int. Cl.
*C07K 1/13* (2006.01)
*C07K 1/04* (2006.01)
*C07D 263/02* (2006.01)

(52) U.S. Cl. ................... 530/403; 530/405; 530/406; 548/215

(58) Field of Classification Search ............ 435/7.1; 436/815, 823; 530/389.8, 402, 403, 405, 530/409; 548/225, 230; 568/307, 317
See application file for complete search history.

(56) References Cited

U.S. PATENT DOCUMENTS

| | | | |
|---|---|---|---|
| 3,957,766 | A | 5/1976 | Berger et al. |
| 3,994,882 | A | 11/1976 | Hirao et al. |
| 4,500,516 | A | 2/1985 | Grinberg et al. |
| 4,794,120 | A | 12/1988 | Manoury et al. |
| 5,086,068 | A | 2/1992 | Raleigh et al. |
| 2003/0166645 | A1 | 9/2003 | Ala et al. |

OTHER PUBLICATIONS

Bryant, Christopher & Deluca, Marlene, Purfication and Characterization of an Oxygen-insensitive NAD (P) H Nitroreductase from Enterobacter cloacae, The Journal of Biological Chemistry, Mar. 5, 1991, vol. 266, No. 7, pp. 4119-4125, The American Society for Biochemistry and Molecular Biology, Inc. USA.
Enzymatic Assay of Diaphorase, May 17, 1998.
Vroomen, LHM, In vivo and in vitro metabolic studies of furazolidone, Wageningen Dissertation Abstracts, WAU Dissertation No. 1182, Nov. 24, 1987.
R-Biopharm, Ridascreen, Nitrofuran (AMOZ), retrieved from the Web Feb. 9, 2004, www.r-biopharm.com/foodandfeed/ridascreen_nitrofuran_amoz.php, pp. 1-2.
Takino, Masahiko, Determination of the Metabolites of Nitrofuran Antibacterial Drugs in Chicken Tissue by Liquid Chromatograph-Electrospray Ionization-Mass Spectrometry (LC-ESI-MS) Application www.agilent.com/chem, Mar. 19, 2003, pp. 1-9, Agilent Technologies, Inc. USA.
Bryant, D.W., McCalla, D.R., Leeksma, M., & Laneuville, P. Type I nitroreductases of *Escherichia coli*, Canadian Journal of Microbiology, vol. 27, pp. 81-86, 1981, Canada.
Ridascreen Nitrofuran (AOZ), Art No. R3701, R-Biopharm AG, Darmstadt, Germany, pp. 1-34, 2002.
Tatsumi, Kiyoshi, Nakabeppu, Hitoshi, Takahashi, Yoshihiro & Kitamura, Shigeyuki, Metabolism in Vivo of Furazolidone: Evidence for Formation of an Open-Chain Carboxylic Acid and @-Ketoglutaric Acid from the Nitrofuran in Rats Archives of Biochemistry and Biophysics, vol. 234, No. 1, pp. 112-116, 1984, Academic Press, Inc.
State Institute for Quality Control of Agricultural Products (RIKILT) Wageningen, & Department of Toxicology of the Agricultural University, TNO-Institute of Animal Nutrition and Physiology The Netherlands, Nov. 1987, pp. 1-158.
Cooper, K.M., Caddell, A., Elliott, C.T., Kennedy, D.Glenn, Analytica Chimica Acta 520 (2004) pp. 79-86, Production and Characterisation of polyclonal antibodies to a derivative of 3-amino-2-oxazolidinone, a metabolite of the nitrofuran furazolidone, United Kingdom, Elsevier B.V.
Newcombe, P.J., & Norris, R.K., Stereolectronic Control of the Rate of Ring Opening in Azidofurans, Tetrahedron Letters, vol. 22, pp. 699-700, Pergamon Press, Ltd, 1981, Great Britain.
Povazanec, F., Kovac, J., & Hesek, D., Collection Czechoslov. Chem. Commun, vol. 45, pp. 150-153, 1980, Czech Republic Opening of the Furan Ring in 5-Azido-2-Furaldehyde.
Hoogenboom, L.A.P., Kammen Van, M. Huveneers-Oorsprong, MBM, Kuiper, H.A., Study on the Role of Glutathione in the Biotransformation and Toxicity of Furazolidone Using Pig Hepatocytes, Toxic. in Vitro, vol. 6, No. 3, pp. 227-237, 1992, Great Britain Pergamon Press, Ltd.
Vass, M., Kotkova, L., Diblikova, I., Nevorankova, Z., Cooper, K.M., Kennedy, D.G., & Franek, M., Production and characterization of monoclonal antibodies for the detection of AOZ, a tissue bound metabolite of furazolidone, pp. 300-310, Czech Republic, 2005.
Diblikova, I., Cooper, K.M., Kennedy, D.G. & Franek, M., Monoclonal antibody-based ELISA for the quantification of nitrofuran metabolite 3-amino-2-oxazolidinone in tissues using a simplified sample preparation, Analytica Chimica Acta(540) 2005, pp. 285-292, Elsevier B.V.

(Continued)

*Primary Examiner*—Shafiqul Haq
(74) *Attorney, Agent, or Firm*—Richard J. Long

(57) ABSTRACT

An antibody and immunogen for generating an antibody to nitrofuran and/or nitrofuran metabolite such as tissue or protein bound nitrofuran metabolites. Nitrofurans and and/or nitrofuran metabolites in a biological sample can be detected by contacting the sample with the antibodies to form a complex that can be detected. The antibodies may also be incorporated into test kits for the detection of nitrofuran and/or nitrofuran metabolites.

5 Claims, No Drawings

OTHER PUBLICATIONS

Cooper, K.M., Elliott, C.T., & Kennedy, D.G., Detection of 3-amino-2-oxazolidinone (AOZ), a tissue-bound metabolite of the nitrofuran furazolidone, in prawn tissue by enzyme immunoassay Food Additives and Contaminants, vol. 21, No. 9, pp. 841-848, Taylor & Francis Ltd. 2004 United Kingdom.

Raleigh, J.A., & Koch, C.J., Biochemical Pharmacology, vol. 40 No. 11, pp. 2457-2464, 1990, Pergamon Press, Great Britain Importance of Thiols in the Reductive Binding of 2-Nitroimidazoles to Macromolecules.

Raleigh, J.A., Zeman, E.M., Rathman, M., Ladine, J.K., Cline, J.M., & Thrall, D.E., Development of an Elisa for the Detection of 2-Nitroimidazole Hypoxia Markers Bound to Tumor Tissue, Int. Journal of Radiation Oncology, Biol. Phys. vol. 22, pp. 403-405, 1992, Pergamon Press, USA.

Raleigh, J.A., La Dine, J.K., Cline, J.M. & Thrall, D.E., An Enzyme-linked immunoabsorbent assay for hypoxia marker binding in tumours, Br. J. Cancer, pp. 66-71, 1994, USA.

Thrall, D.E., McEntee, M.C., Cline, J.M., & Raleigh, J.A., Elisa Quantification of CCI-103F Binding in Canine Tumors Prior to and During IRadiation, Int. J. Radiation Oncology Biol. Phys. vol. 28, No. 3, pp. 649-659, 1994, Elsevier Science, Ltd. USA.

Joseph, P., Jaiswal, A.K., Stobbe, C.C., & Chapman, J.D., The Role of Specific Reductases in the Intracellular Activatation and Binding of 2-Nitroimidazoles, Int. J. Radiation Oncology Biol. Phys., vol. 29, No. 2, pp. 351-355, 1994, Elsevier Science Ltd USA.

Vroomen, L.H.M., Berghmans, M.C.J., Groten, J.P., Koeman, J.H., Van Bladeren, P.J., Reversible Interaction of a Reactive Intermediate Derived from Furazolidone with Glutathione and Protein, Toxicology and Applied Pharmacology, 95, pp. 53-60, 1988, Academic Press, Inc.

Ebetino, F.F., Carroll, J.J., & Gever, G., Reduction of Nitrofurans I. Aminofurans, May 1962, vol. 5, pp. 513-524.

Beckett, A.H., & Robinson, A.E., The Reactions of Nitrofurans with Bacteria -II. Reduction of a Series of Antibacterial Nitrofurans by Aerobacter aerogenes, Journal of Medicinal and Pharmaceutical Chemistry, vol. 1, No. 2, pp. 135-152, 1959.

Hoogenboom, L.A.P., Kammen, M Van, Berghmans, M.C.J., Koeman, J.H. & Kuiper, H.A., The Use of Pig Hepatocytes to Study the Nature of Protein-Bound Metabolites of Furazolidone: A New Analytical Method for their Detection, Fd Chem. Toxic, vol. 29, No. 5, pp. 321-328, 1991, Pergamon Press.

Kazanis, S. & McClelland, R.A., Electrophilic Intermediate in the Reaction of Glutathione and Nitrosoarenes, American Chemical Society, J. Am. Chem. Soc., vol. 114, No. 8, pp. 3052-3059, 1992.

Silva, J.M., Khan, S., & O'Brien, P.J., Molecular Mechanisms of Nitrofurantoin-Induced Hepatocyte Toxicity in Aerobic versus Hypoxic Conditions, Archives of Biochemistry and Biophysics, vol. 305, No. 2, pp. 362-369, 1993, Academic Press, Inc.

Mattamal, M.B., Zenser, T.V., Palmier, M.O., & Davis, B.B., Renal Reduced Nicotinamide Adenine Dinucleotide Phosphate: cytochrome c Reductase-mediated Metabolism of the Carcinogen N-[4-(5-Nitro-2-furyl )-2-thiazolyl]acetamide, Cancer Research, vol. 45, pp. 149-156, Jan. 1985, USA.

Folker Lieb & Karl Eiter, Nucleophile Substitutionsreaktionen am 5-Nitro-2-furfurol, Liebigs Ann. Chem, vol. 761, pp. 130-136, 1972, Germany.

Miller, C., Folkes, L.K., Mottley, C., Wardman, P. & Mason, R.P., Revisiting the Interaction of the Radical Anion Metabolite of Nitrofurantoin with Glutathione, Archives of Biochemistry and Biophysics, vol. 397, No. 1, Jan. 2002, pp. 113-118, Elsevier Science, Ltd. USA.

Gottschall, D.W., & Wang, R., Depletion and Bioavailability of [14C] Furazolidone Residues in Swine Tissues, J. Agric. Food Chem. vol. 43, 9pp. 2520-2525, 1995, USA.

Hoogenboom, L.A.P., Polman, TH.H.G., Lommen, A., Huveneers, M.B.M. & Vanjrhijn, J., Biotransformation of furaltadone by pig hepatocytes and *Salmonella typhimurium* TA 100 bacteria, and the formation of Protein-bound metabolites, Xenobiotica, vol. 24, No. 8, pp. 713-727, 1994, Taylor & Francis, Ltd.

Horne, E., Cadogan, A., O'Keeffe, M.O., & Hoogenboom, L.A.P., Analysis of Protein-bound Metabolites of Furazolidone and Furaltadone in Pig Liver by High-performance Liquid Chromatography and Liquid Chromatography-Mass Spectrometry, Analyst, vol. 121, pp. 1463-1468, 1996.

McCalla, D.R., Reuvers, A. & Kaiser, C., Mode of Action Nitrofurazone, Journal of Bacteriology, vol. 104, No. 3, pp. 1126-1134, 1970, American Society for Microbiology, USA.

John L. Wong, Yu Ting Zheng, Junyu Li, Carlo H. Tamburro and Frederick W. Benz; Immunoassay of haemoglobin - acrylonitrile adduct in rat as a biomarker of exposure; Biomarkers; Jul. 1998; pp. 317-326; vol. 3, Issues 4 & 5.

J.L. Wong, D.Z. Liu and Y.T. Zheng; Lysine conjugate of acrylonitrile as antigenic sites in hemoglobin adducts; Journal of Peptide Research; 2004; pp. 171-174; vol. 63, No. 2.

METHOD AND ANTIBODIES FOR DETECTING NITROFURAN

This application claims priority to, and is a continuation of, PCT/US06/32443, filed Aug. 21, 2006, which further claims priority to U.S. Provisional Application 60/710,026, filed Aug. 19, 2005, both of which are hereby incorporated by reference. This application claims priority to, and is a continuation-in-part of, PCT/US05/12898, filed Apr. 15, 2005, which further claims priority to U.S. Provisional Application 60/563,340, filed Apr. 19, 2004; U.S. Provisional Application 60/563,779, filed Apr. 20, 2004; and U.S. Provisional Application 60/565,364, filed Apr. 26, 2004, all of which are hereby incorporated by reference.

BACKGROUND

Nitrofurans are synthetic broad-spectrum antibiotics used in animal, aquaculture and honey production. Nitrofurans are antibacterial, antiprotozoan and growth promoters. In animal studies the parent drugs and their metabolites showed carcinogenic and mutagenic characteristics. For that reason, nitrofuran use in the treatment of animals used for food production is prohibited. Despite such bans, residues continue to appear in the food supply. In particular, metabolites of nitrofurans can be tissue or protein bound resulting in residue remaining long after administration of the parent drug.

Common parent nitrofuran drugs, and their respective side chains (the R groups), include: furazolidone (side chain: 3-amino-2-oxazolidinone=AOZ), furaltadone (side chain: 3-amino-5-morpholinomethyl-2-oxazolidinone=AMOZ), nitrofurantoin (side chain: 1-aminohydantoin=AHD) and nitrofurazone (side chain: semicarbazide=SEM). The structures are as follows:

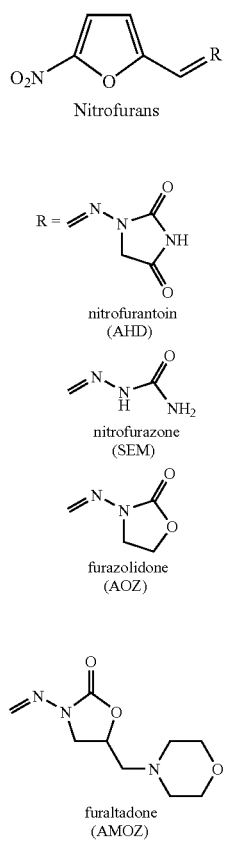

Nitrofurans are rapidly metabolized. The in situ half-life can be less than two hours. During metabolism, the nitrofuran parent may be reduced, such as by one or more nitroreductases. In one such scenario, the basic nitrofuranyl moiety (the common portion attached to the R group), is transformed into a different chemical group, while the R group (on the right hand side of the nitrofuran parent structure) remains intact.

Several methods for determining the use of a nitrofuran parent drug are via indirect metabolite detection. Such methods include liquid chromatography with ultra violet detection (LC-UV), liquid chromatography with mass spectrometer detection (LC-MS), liquid chromatography with tandem mass spectrometer detection (LC-MS/MS) and immunodiagnostics. The metabolite can be protein bound and, therefore, a hydrolysis step is used to cleave the side chain.

For UV detection, the released side chain can form a hydrazone derivative with 2-nitrobenzaldehyde. For example, in the cases of furazolidone and furaltadone, hydrazones with the acronyms of NPAOZ and NPAMOZ, respectively, are formed by the above process. It is the hydrazones—NPAOZ and NPAMOZ—not the actual metabolite, that are targeted for detection. Those hydrolysis and derivatization reactions require 16-24 hours prior to sample detection.

SUMMARY

One aspect is a method and test kit that rapidly detects the use of a nitrofuran in food and/or food producing animals. Test times can be less than one to two hours including any required extraction procedures. A related aspect is rapidly detecting a nitrofuran parent drug and/or nitrofuran metabolite, for example the protein or tissue bound metabolite of one or more nitrofuran metabolites, in a sample.

Another aspect includes antibodies, and methods of producing antibodies, with affinity to a nitrofuran metabolite, such as tissue or protein bound metabolite. Such antibodies may also have affinity to nitrofuran parent drug. By the terms antibody and antibodies we include polyclonal or monoclonal antibodies and antibody fragments. Tests or methods to detect multiple nitrofurans or metabolites may include combinations of antibodies. The antibodies can have affinity to particular nitrofurans or in some cases be cross-reactive to multiple nitrofuran metabolites.

Another aspect is to provide an immunogen for raising antibodies to nitrofurans and/or metabolites of a nitrofuran, such as the tissue or protein bound metabolites of a nitrofuran. The immunogen can have a structural moiety common to at least two nitrofuran metabolites, for example a common structural portion relative to at least two protein or tissue bound nitrofuran metabolites. Depending upon the portion of the structure against which the antibody is raised, the antibody may have cross-reactivity to multiple metabolites or be relatively specific to a single nitrofuran and/or metabolite. That is, antibody to the region common to multiple metabolites may be cross-reactive whereas antibody to the uncommon region may be relatively specific. An example of an immunogen can include a portion deriving from an acrylonitrile, such as a 4-oxo-pent-2-enenitrile derivative of a nitrofuran, the structure of which is:

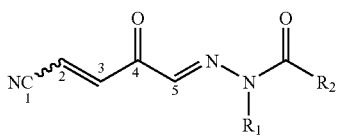

The above acrylonitrile can be used to produce an immunogen or portion of an immunogen with the structure:

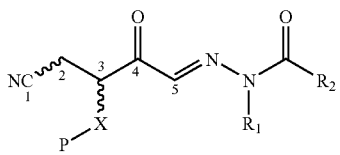

wherein X can be, for example, a nucleophile such as —S— or —NH— or —O—; wherein P can be a peptide, protein, nucleic acid, polysaccharide or small molecular biochemical covalently linked to a protein; wherein $R_1$ can be H or part of a heterocyclic ring structure such as a heterocyclic ring structure with an unsubstituted two-carbon chain, part of a heterocyclic ring structure of a two-carbon chain with an oxo (=O), 4-morpholinomethyl, or a 5 or 6 membered heterocyclicalkyl ring substitution; and wherein $R_2$ can be, for example, NH and O when enclosed in a heterocyclic ring said heterocyclic ring including $R_1$, or $NH_2$ when part of a linear side chain.

Another aspect is an immunogen for raising antibodies to a nitrofuran and/or metabolites thereof, such as a tissue or protein bound metabolite, the immunogen produced by enzymatically derivatizing a nitrofuran parent. Enzymatic derivatization can include use of enzymes, such as nitroreductase enzymes, that may be part of the natural metabolic breakdown of nitrofurans in vivo. Such an enzymatic derivative, or enzymatic metabolite, can be combined with a carrier protein for use as an immunogen.

Another aspect is a method and test kit, such as a lateral flow chromatographic assay, for detecting a nitrofuran and/or nitrofuran metabolite, such as a tissue or protein bound metabolite, in an animal derived biological sample such as honey, shrimp, shrimp homogenate or an extract thereof. The test kit and method can include a mobile phase composition having a first labeled antibody that can bind to at least one nitrofuran and/or metabolite. The labeled first antibody can be produced using an immunogen comprising a chemical structure with a structural moiety common to at least two nitrofuran metabolites, such as an acrylonitrile derivative. The labeled first antibody can also be produced using an enzymatically derived nitrofuran metabolite such as a protein bound nitrofuran metabolite. A stationary-phase membrane can be in contact or contacted with the mobile-phase composition. The stationary-phase membrane can have a first end and a second end. A test zone on the membrane can have a binder bound to the membrane. The binder can have affinity to the first labeled antibody and be capable of competing with nitrofuran and/or metabolite in the sample for binding to the first labeled antibody. In such a test kit and method the binding of said first labeled antibody to the membrane bound binder in the test zone can provide a detectable signal. The test kit and method may also include a control zone having a second binder bound to the membrane. The second binder can have affinity to said first labeled antibody, to provide a signal that the test is complete and for comparison to the signal of the test zone. Alternatively, in such a test kit and method, the labeled first antibody can be capable of binding with multiple nitrofurans and/or metabolites, for example two protein or tissue bound nitrofuran metabolites. In another embodiment, multiple antibodies can be used each with affinity to individual nitrofuran metabolites.

The method and test kit may also be in the form of an enzyme linked immunosorbant assay (ELISA) in which the herein described antibodies are used to bind nitrofuran metabolite. Such ELISA assays can include a multiwell assay in which multiple antibodies are used, one in each well, or combined together in a well, including a combination of enzymatically derived and synthetically derived antibodies in separate wells.

Another aspect is a compound and a method of synthesizing a compound, with the formula:

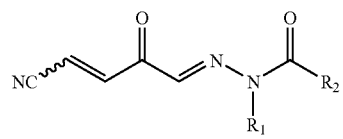

wherein $R_1$ can be, for example, either H or part of a heterocyclic ring structure such as a heterocyclic ring structure of an unsubstituted two-carbon chain, part of a heterocyclic ring structure of a two-carbon chain with an oxo (=O), 4-morpholinomethyl, or a 5 or 6 membered heterocyclicalkyl ring substitution; and wherein $R_2$ can be NH or O when enclosed in a heterocyclic ring said heterocyclic ring including $R_1$, or $NH_2$ when part of a linear side chain. Such a compound is useful in creating an immunogen for raising antibody to the various nitrofuran metabolites. Some specific examples of compounds of this general structure include:

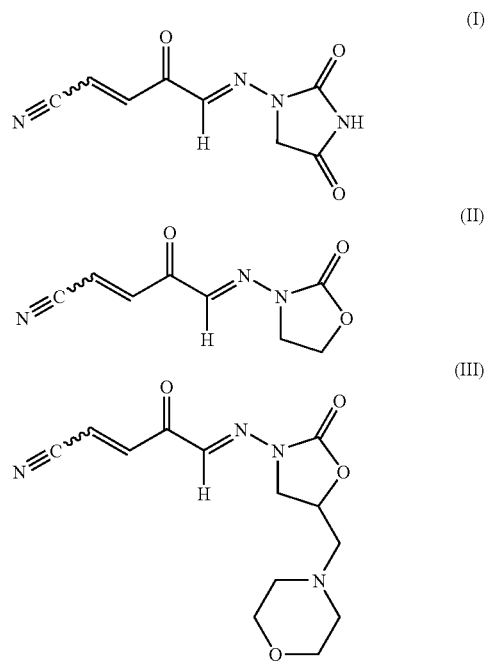

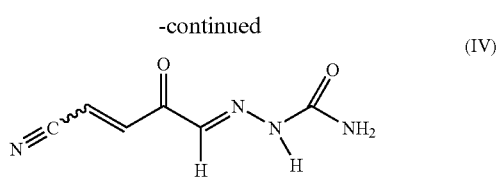
(IV)

Methods of synthesizing the above compounds (I-IV) can include a condensation reaction in the presence of 5-azido-2-furaldehyde and at least one of the following side chains: 1-aminohydantoin; 3-amino-2-oxazolidone; 5-morpholinomethyl-3-amino-2-oxazolidone; and or semicarbazide.

Tissue or protein bound metabolites of nitrofuran that may be used as an immunogen, may include the general base structure of acrylonitrile or 4-oxo-pent-2-enenitrile derivatives. Acrylonitrile derivatives are reactive and can bind covalently to an active nucleophilic group. Such active nucleophilic groups include the —SH, —NH₂ and —OH groups of biochemicals or biopolymers including proteins, nucleic acid and polysaccharides. In the following reaction example, the acrylonitrile binds covalently to cysteine-containing proteins or peptides (such as glutathione) to form the acrylonitrile-Cys-protein or acrylonitrile-glut-protein adduct.

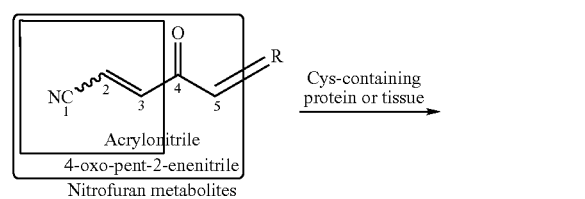

The acrylonitrile derivatives may also form adducts with other amino acid residues, for example to the primary amine group of a lysine side-chain.

Another aspect includes an N-linked NF metabolite conjugate of the following structure:

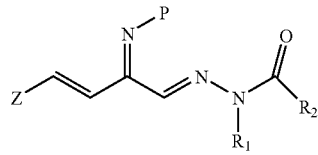

Where P can be a peptide, protein, nucleic acid, polysaccharide or small molecular biochemical alone or covalently linked to a protein; wherein $R_1$ can be H or part of a heterocyclic ring structure such as a heterocyclic ring structure with an unsubstituted two-carbon chain, part of a heterocyclic ring structure of a two-carbon chain with an oxo (=O), 4-morpholinomethyl, or a 5 or 6 membered heterocyclicalkyl ring substitution; and wherein $R_2$ can be, for example, NH and O when enclosed in a heterocyclic ring said heterocyclic ring including $R_1$, or $NH_2$ when part of a linear side chain. Z can be a functional group including but not limited to —CN, —OH, —O—CO2H, halides, carboxylate, —OR where R is an alkyl or acyl group of a low carbon chain and —NHR where R is an alkyl or acyl group of a low carbon chain.

Some embodiments require, prior to testing, separation of the NF metabolite from either or both the matrix or interferences within the matrix. An aspect includes separation by combining the sample with resin, such as ion exchange resin, centrifuging the mixture and testing of the supernatant.

DETAILED DESCRIPTION

An embodiment includes a chemical compound, and method of producing a chemical compound, which is structurally similar, or identical, to a naturally occurring tissue or protein bound nitrofuran metabolite. Such a compound and method can be used in, or as, an immunogen in raising antibodies to various nitrofurans and their metabolites. For example, 5-azido-2-furaldehyde can be condensed, using hydrochloric acid at room temperature or with heating, with: 1-aminohydantoin (AHD), 3-amino-2-oxazolidinone (AOZ), 3-amino-5-morpholinomethyl-2-oxazolidinone (AMOZ), or semicarbazide (SEM) as follows:

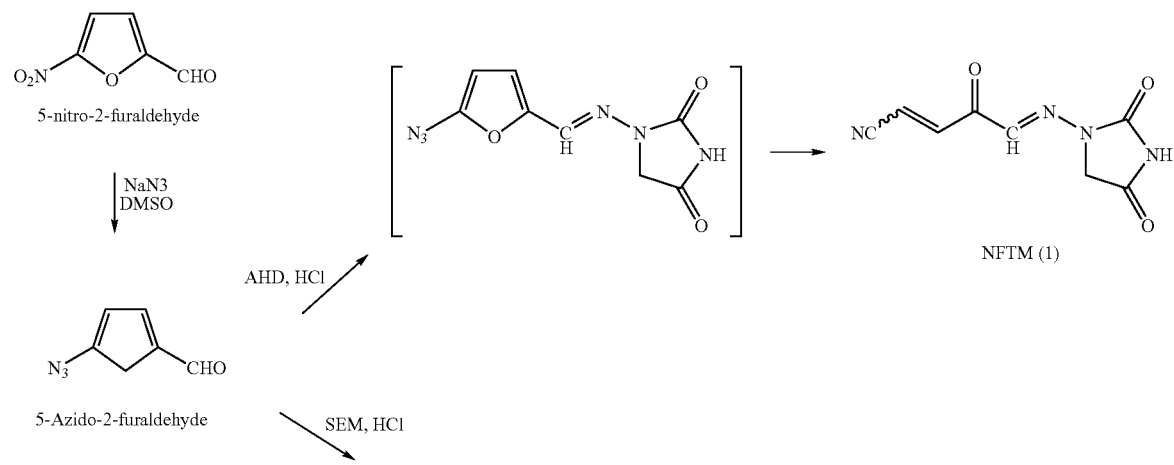

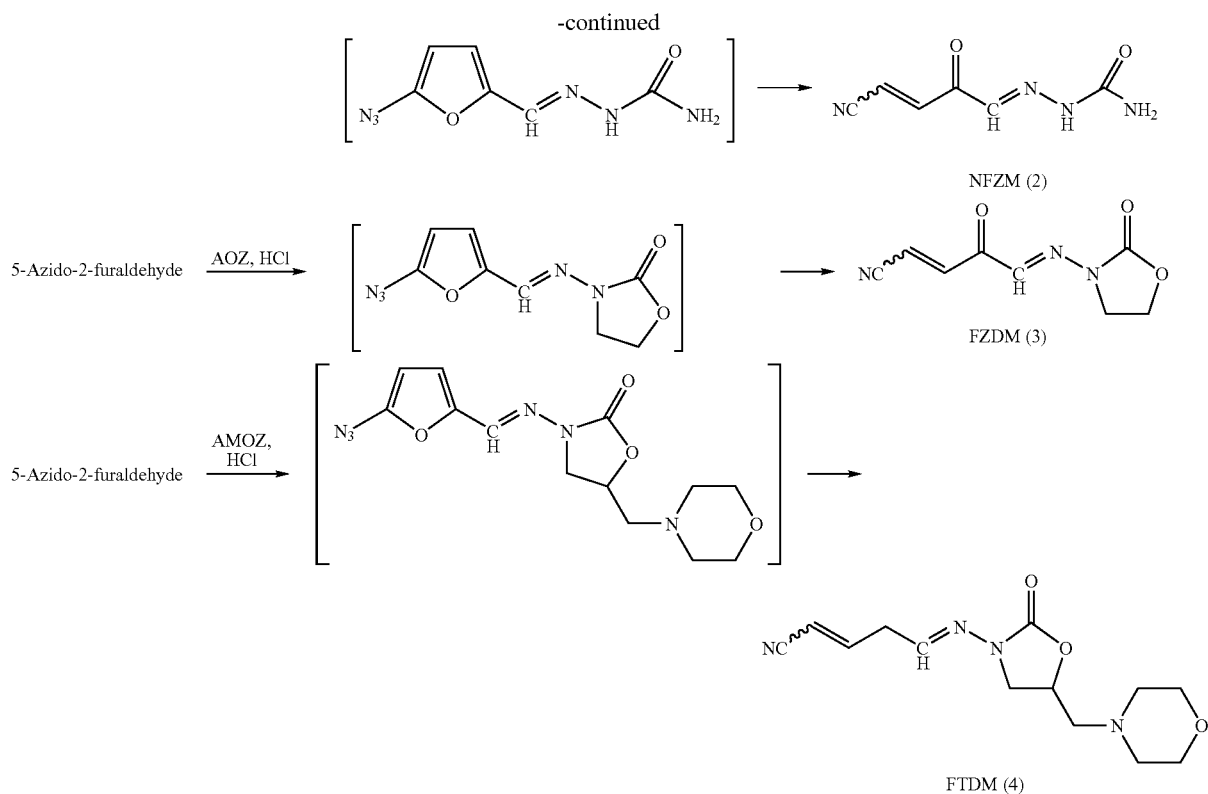

NFZM (2)

FZDM (3)

FTDM (4)

The above condensation reactions can occur in acidic media and can occur with the hydrochloride salt forms of AHD, AOZ, AMOZ and SEM, in an alcohol/water mixture. Each individual condensation reaction forms an unstable intermediate, the form of which is shown in brackets, which can undergo structural rearrangement of the furanyl ring opening to give the corresponding acrylonitrile derivatives: NFTM (1), NFZM (2), FZDM (3), and FTDM (4). The resulting products, compounds 1-4, are the acrylonitrile derivatives of the corresponding nitrofuran drugs. Except for the reaction of 5-azido-2-furaldehyde with AHD, which may require heating at between 50-60 degrees C. to speed up the reaction, the above reactions can be formed at room temperature within one day.

Another embodiment includes the corresponding amino acid, peptide or protein adducts of compounds 1-4 (NFTM, NFZM, FZDM and FTDM). For example, structures of N-acetyl-L-cysteine and N-acetyl-glutathione adducts, including NFTM-Cys (5a), NFTM-Glut (5b), NFZM-Cys (6a) NFZM-Glut (6b), FZDM-Cys (7a), FZDM-Glut (7b), FTDM-Cys (8a) and FTDM-Glut (8b) are as follows:

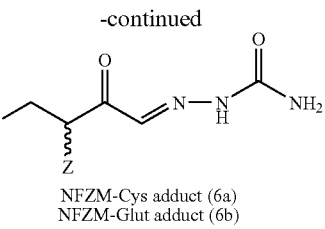

NFZM-Cys adduct (6a)
NFZM-Glut adduct (6b)

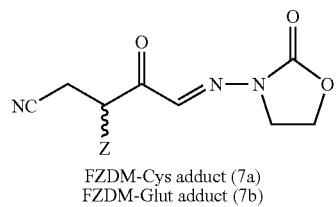

FZDM-Cys adduct (7a)
FZDM-Glut adduct (7b)

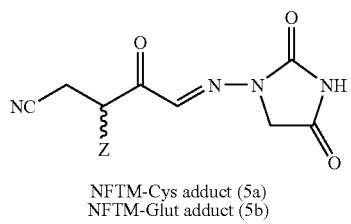

NFTM-Cys adduct (5a)
NFTM-Glut adduct (5b)

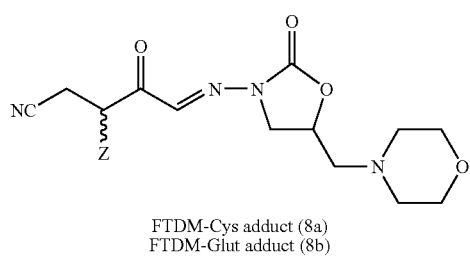

FTDM-Cys adduct (8a)
FTDM-Glut adduct (8b)

-continued

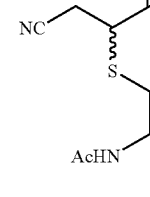
where Z = 
for 5a-8a for 5b-8b

The amino acid, peptide or protein adducts can be used to form conjugates to protein carriers to be used in or as an immunogen and include the general structure of:

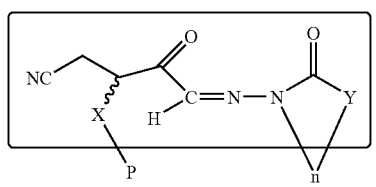

wherein Y can be —NH or —O— when enclosed in a heterocyclic ring, or —NH$_2$ as part of a linear side chain; X can be —S—, —NH— or —O—. In the portion outside of the box shown above, P can include a biopolymer including peptide, protein, nucleic acid, or polysaccharide, that originally contains free sulfhydryl (—SH) or amino (—NH$_2$) or hydroxyl (—OH) groups that contributes the X linkage in forming the adducts with the metabolites. P can also be a small molecular biochemical such as the sulfhydryl-containing glutathione or a bifunctional cross-linker that can be subsequently linked to a biopolymer. -n- can be part of the heterocyclic ring structure comprising a two-carbon chain with or without an oxo (=O), 4-morpholinomethyl, or a 5 or 6-membered heterocyclic alkyl ring substitution.

Other embodiments include acrylonitrile-lysine-peptide/protein adducts and acrylonitrile beta alanine adducts, and methods of forming such adducts. The adducts can be combined, with appropriate coupling agents such as dicyclohexyl carbodiimide (DCC) and N-hydroxysuccinimide (NHS), to produce the corresponding protein conjugates for use as or as part of an immunogen. One possible reaction to produce protein conjugates is:

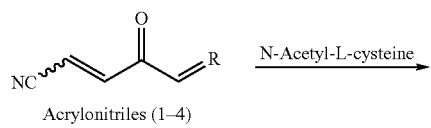
Acrylonitriles (1–4)    N-Acetyl-L-cysteine →

-continued

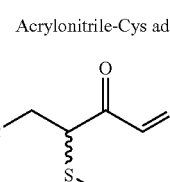
Acrylonitrile-Cys adducts (5a–8a)

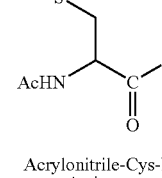
Acrylonitrile-Cys-NHS
Active ester

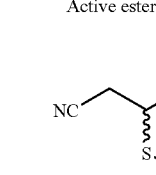
S-linked acrylonitrile-Cys
protein conjugates (9a–d)

| R |
|---|
| a, AHD |
| b, SEM |
| c, AOZ |
| d, AMOZ |

Another possible reaction to produce a protein conjugate is:

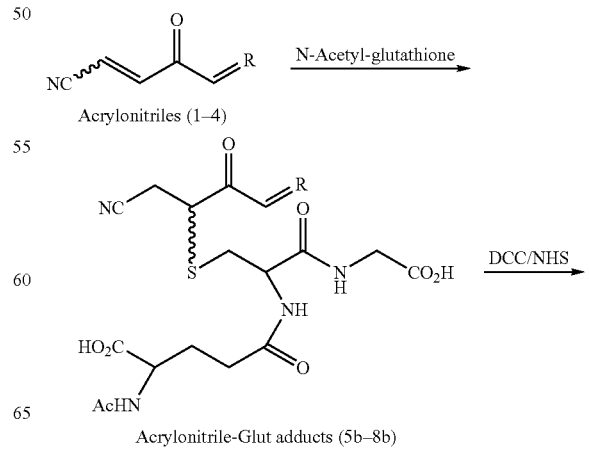
Acrylonitriles (1–4)

Acrylonitrile-Glut adducts (5b–8b)

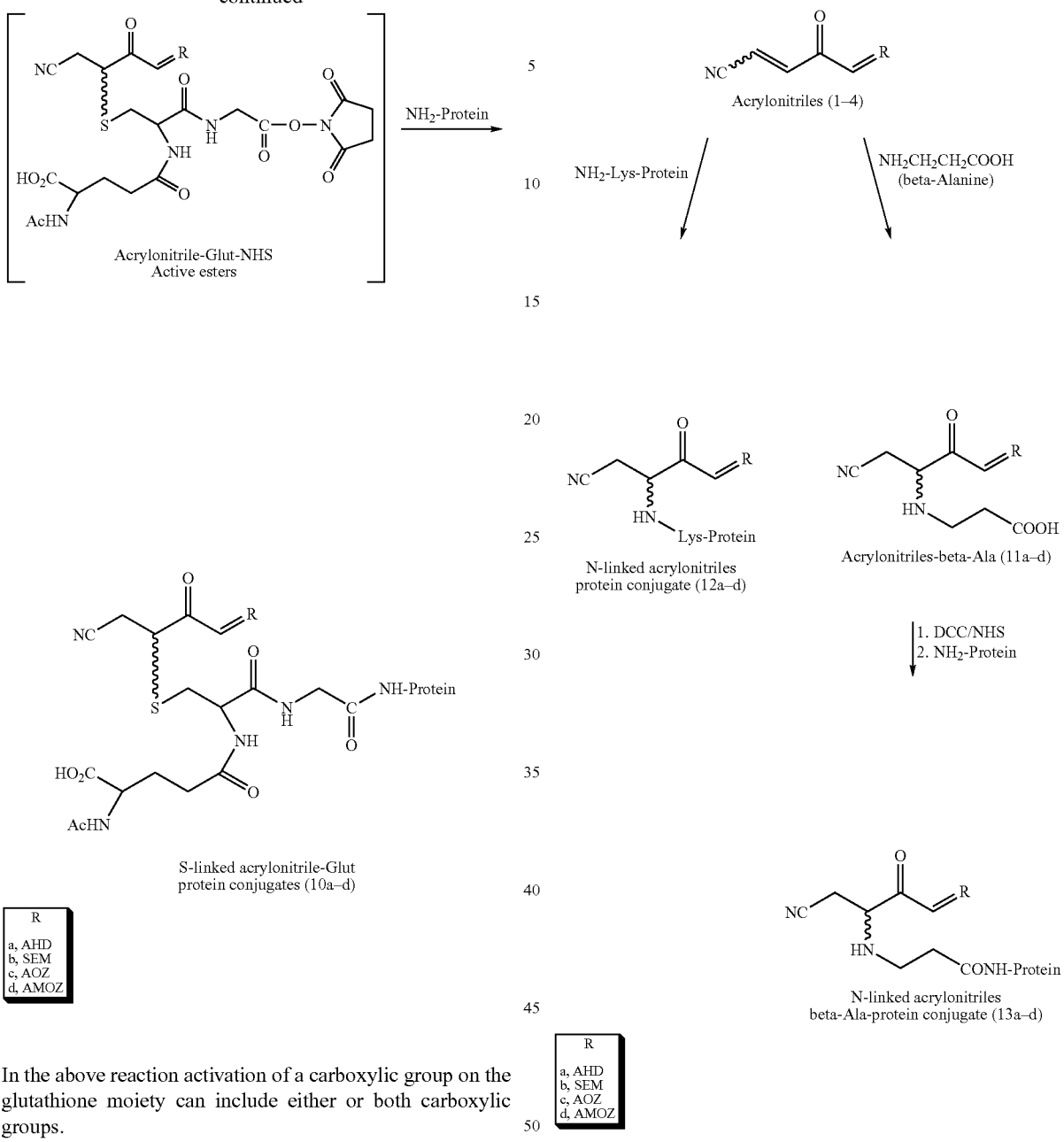

In the above reaction activation of a carboxylic group on the glutathione moiety can include either or both carboxylic groups.

In another embodiment a bifunctional cross-linker, for example having a thiol group at one end and another reactive chemical group at the other end, can be used to form the acrylonitrile-cross-linker adduct. Many suitable bifunctional cross-linkers are well known and commercially available.

The acrylonitrile-cysteine adducts can be replaced isosterically, such as with an acrylonitrile-amino compound adduct. In an example, an acrylonitrile-beta-alanine adduct is formed, as shown below, to produce compounds 11a-d. The acrylonitrile-beta-alanine adducts carry a free carboxylate group useful for forming protein/peptide conjugates such as compounds 13a-d shown below. In another example, direct conjugates between the acrylonitriles and cationized bovine serum albumin (cBSA) are formed, as shown below, to produce compounds 12a-d.

Conjugates can also be formed using, for example, N-Succinimidyl 3-(2-pyridyldithio)propionate (SPDP) or 2-iminothiolane (2-IT) to form the bridges. For example, SPDP and/or (2-IT) can react with the protein carriers first. In the case of SPDP, after its succinimidyl end is conjugated to the protein, the 2-pyridyldisulfide terminus can be deprotected with DTT (dithiolthreitol) to expose the free thiol end, followed by desalting to remove the excess of thiol-containing DTT and coupling with the acrylonitrile. In the case of 2-iminothiolane (2-IT), the reagent reacts with the primary amines of protein to result in the ring opening of 2-IT and the simultaneous exposure of the free thiol end which then reacts with the acrylonitriles to complete the bridging. Typical SPDP and 2-IT bridge reactions are:

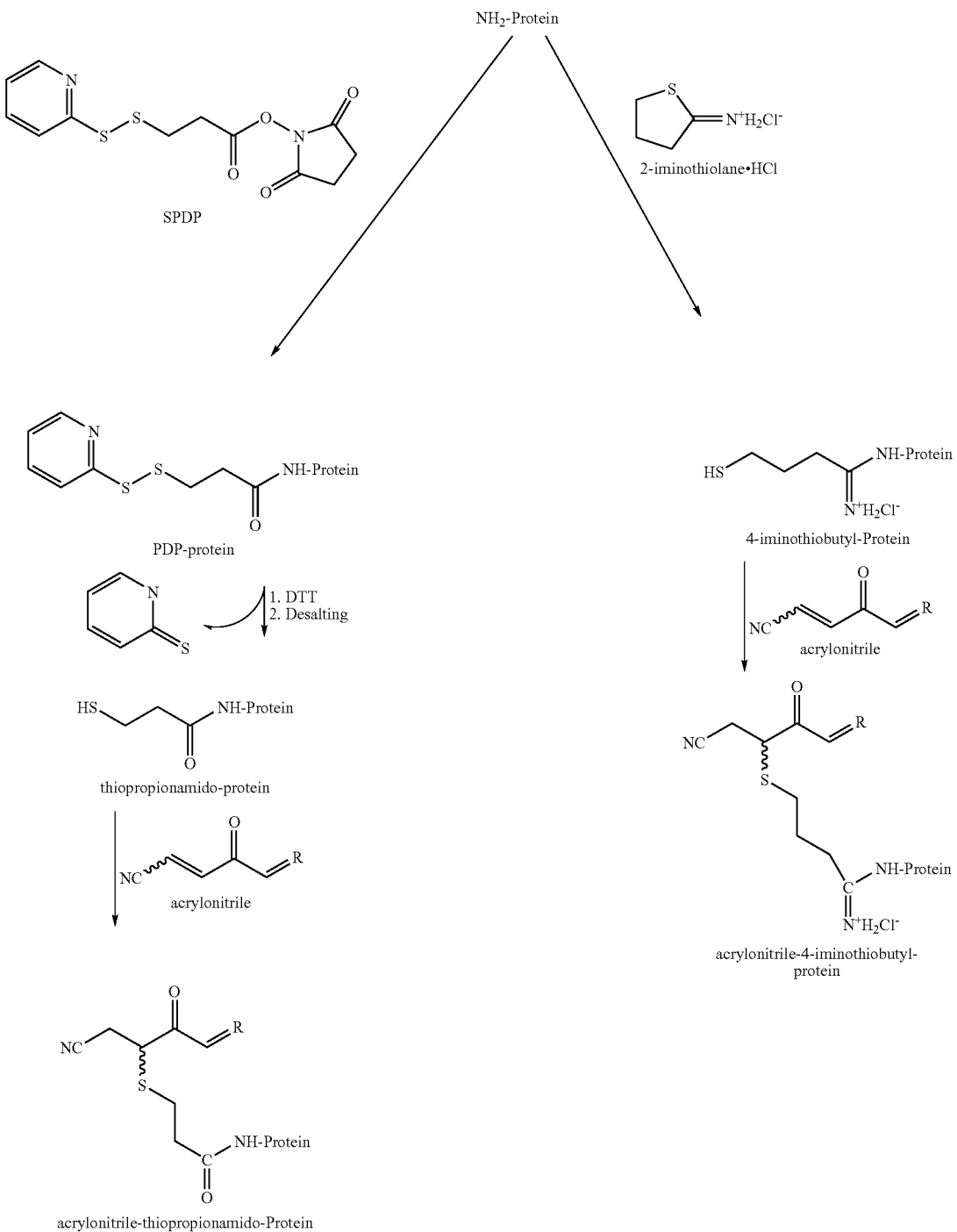

We have described several possible ways to form the S-linked and N-linked acrylonitrile protein conjugates. Many other possible linkage constructs will be obvious to those skilled in the art of bioconjugation.

Another approach to preparing an acrylonitrile derivative for immunogen preparation is by a hydrogenation reaction of the parent nitrofurans, catalyzed by a metal such as palladium, nickel, rhodium or platinum, or in accordance with hydrogenation procedures well known to those skilled in the art. The hydrogenation reaction is preferably stoichiometrically controlled so that only two moles of hydrogen per mole of nitrofuran are taken up to form the acrylonitriles.

In an embodiment not relying on control of hydrogenation, the over-reduced 4-cyano-2-oxobutyraldehyde semicarbazone derivative product can be converted back to the acrylonitrile derivative, for example by bromination using N-bromosuccinimide, followed by dehydrohalogenation (elimination of the bromine and double bond formation) as follows:

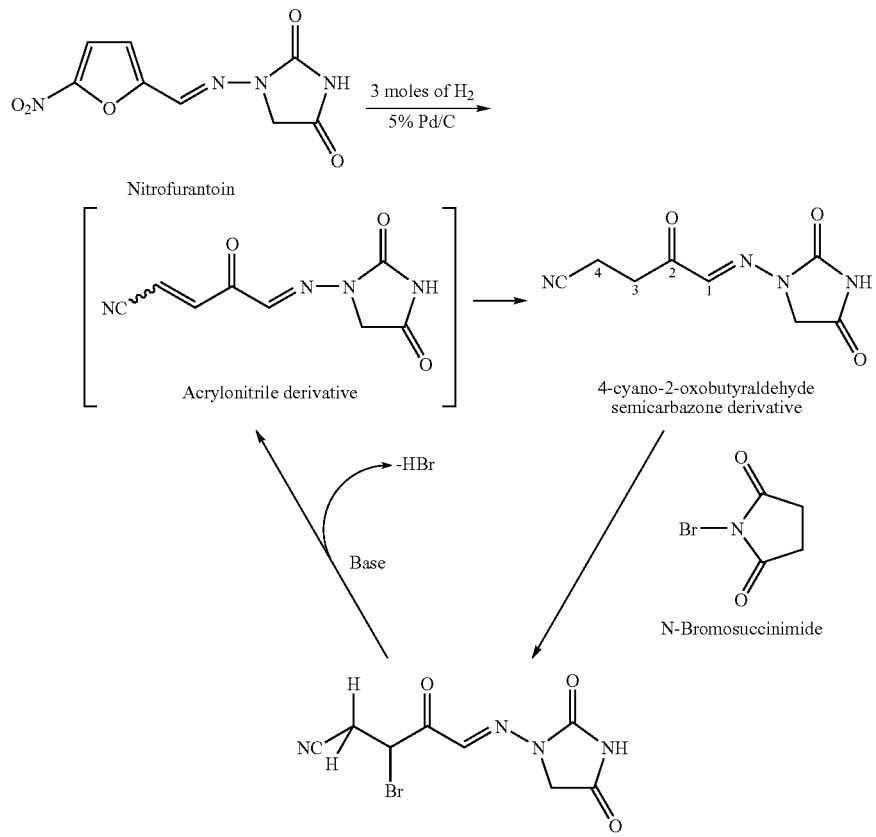

In another embodiment a protein-bound nitrofuran metabolite, such as for use as or in an immunogen, is obtained through enzymatically derivatizing the parent nitrofuran and binding of the derivative to a protein. A variety of reductase enzymes, including those known as nitroreductases, are useful. Such enzymes can be from prokaryotic or eukaryotic sources. In an example, diaphorase from *Clostridium kluyveri* was used. Other well known useful sources of nitroreductases enzyme includes *Salmonella typhimurium*, hepatocytes such as pig hepatocytes, microsomes such as pig-liver microsomes or rat-liver microsomes, *Enterobacter cloacae, Bacteroides fragilis, Escherichia coli* and *Aerobacter aerogenes*. Some specific useful enzymes are known as microsomal NADPH cytochrome P-450-reductase, mitochondrial and microsomal NADH-cytochrome-b5-reductase, cytosolic xanthine oxidase, aldehyde oxidase, DT-diaphorase (NADPH-dehydrogenase) and lipoyldehydrogenase (diaphorase II). The nitrofuran can be nitroreduced, for example into an open-chain acrylonitrile, while being incubated with a protein such as keyhole limpet hemocyanin (KLH) or *Bacillus thuringiensis israelensis* (BTI) to produce the protein bound metabolite that can be used as, or in, an immunogen.

In another embodiment a protein-bound nitrofuran metabolite for use as, or in, an immunogen is biologically derived and isolated using an affinity column or other chromatographic methods. The source of said biologically derived protein-bound nitrofuran metabolites can be the protein fraction of nitrofuran incurred or known contaminated samples, for example samples from seafood such as shrimp or honey, poultry and other animal tissues. Protein fractions from nitrofuran incurred samples can be obtained through a variety of methods including: enzyme digestion, centrifugation, dilution, precipitation, filtration, desalting, and concentration.

An example of a technique of obtaining protein fractions from incurred samples involves affinity column preparation and isolation of biological materials via specific binding. Such techniques can be used to isolate the biologically derived protein bound metabolite. One such technique includes immobilizing (via covalent attachment) onto affinity resin an antibody or natural receptor that recognizes and binds specifically to a nitrofuran R group. By passing a water soluble protein fraction, obtained from an incurred sample (an exemplified procedure of protein fraction preparation is described herein below), it is possible to: (a) capture the protein-bound nitrofuran metabolites on a column packed with said antibody-bound affinity resin; (b) wash away proteins and other biopolymers that are not associated with nitrofuran metabolites; and (c) release the protein-bound nitrofuran metabolites from the affinity column thereby achieving isolation and enrichment of the desired protein-bound nitrofuran metabolite. Alternatively, the target protein can be eluted and the non-target proteins and other non-target molecules bound to the column. The isolated protein bound metabolite can be useful for further antibody generation and/or for use as a positive standard.

In an example of a method for producing antibodies specific for the individual side chains (R groups), a protein conjugate immunogen, with multiple attachments of individual R groups can be prepared. The protein conjugates can be prepared via (a) direct condensation of whole molecules of AHD, SEM, AOZ or AMOZ with an aldehyde compound that also contains, preferably, an additional functional group (for the ease of further derivatizing and coupling to protein carriers), or (b) acid hydrolysis of a parent hydrazone compound containing an AHD, SEM, AOZ or AMOZ side chain (such as in the nitrofuran drugs) to release the side chain which then condenses with said aldehyde compound present in large excess to obtain the functionalized derivatives of those R groups. As shown in the following reaction scheme, functionalized aldehyde compounds include a benzaldehyde substituted with an electron-withdrawing (EW) group such as nitro (e.g. 2- or 4-nitrobenzyaldehyde), carboxylate, halogens and cyano groups.

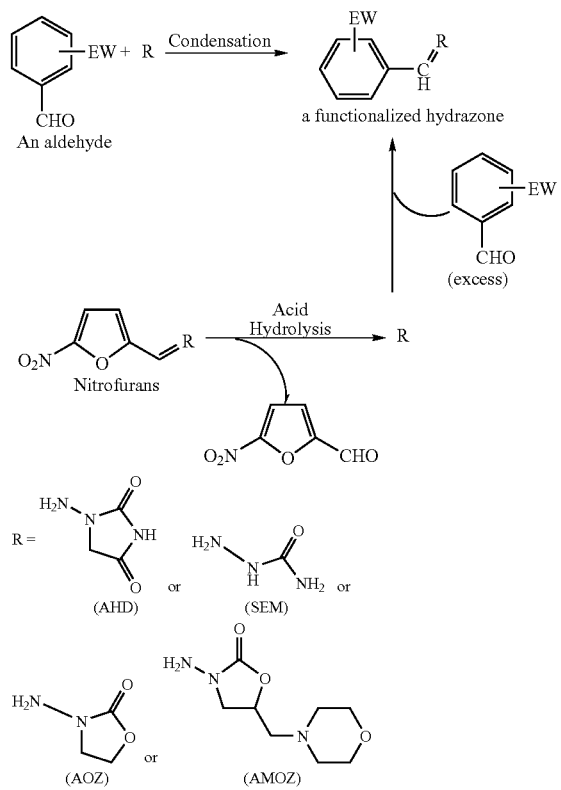

The above EW group not only can facilitate the condensation of free or released AHD, SEM, AOZ and AMOZ with the aldehyde in an acid-catalysis reaction, but also can allow the resulting new hydrazones to be directly or indirectly (via additional conversion steps) coupled with protein carriers. Techniques and methods of those conversions are well known in organic chemistry. One such technique is the conversion of the nitro group in the resulting nitrobenz-hydrazones to an amino group by catalytic hydrogenation. Said amino group can then react with a cyclic anhydride (e.g. succinic or glutaric anhydride) to form, as shown below, a hemisuccinate (succinimido) or hemiglutarate (glutaramido) derivative of the benzhydrazones. With the built-in free carboxylate, the succinamido-benzhydrazone can be coupled to protein carriers via the use of coupling reagents well known to those skilled in the arts.

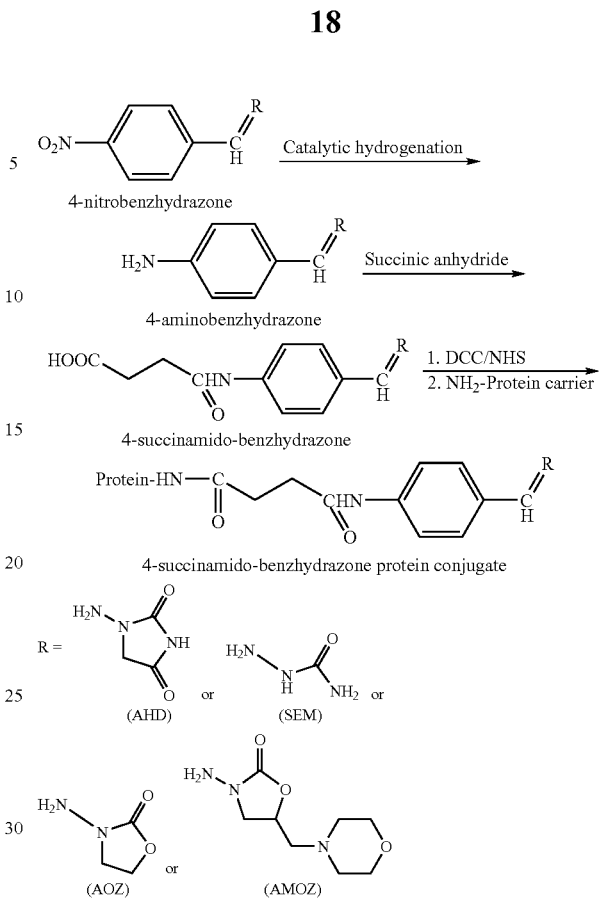

Any of the immunogens described below can be used to immunize rabbits or other appropriate animals, such as mice, in accordance with standard immunization protocols for polyclonal antisera or monoclonal antisera production.

The antibodies produced through the herein described methods may be useful for immunoassays for veterinary drug monitoring of nitrofurans. Various immunoassay formats and methods that are well known in the art can be adopted including ELISA's, visibly labeled lateral flow chromatographic, cytochemical and fluorescent, direct or indirect methods and sandwich and competitive inhibition assays.

Various embodiments include an ELISA format. Several ELISA formats are possible including adsorbing the antibody to an inert surface, for example a 96-well polystyrene plate. After adsorption of the antibody, the surface is washed with a solution of an appropriate blocking agent, for example casein from non-fat dry milk powder. Sample can be added to the well, after adsorption and washing as described above, followed by the nitrofuran-metabolite tracer or sample can be combined with nitrofuran-metabolite tracer and added with tracer to the plate. The tracer can be either nitrofuran metabolite directly labeled with an enzyme or indirectly, for example utilizing a biotin/avidin bridge. For example avidin-enzyme conjugate preparations are commercially available. Such a preparation can be used with a synthetically prepared biotin-X-nitrofuran-metabolite conjugate (X referring to a bi-functional cross-linker). Analyte in the sample (nitrofuran metabolite) competes with tracer to bind to the immobilized (or coated) antibody. After washing, the surface is treated with a substrate that forms a colored product when contacted with the bound enzyme tracer. Color intensity is inversely related to the amount of analyte present.

In another example of an ELISA format, an analyte competitor, such as nitrofuran metabolite-Cys-BSA, is adhered to the surface of the 96-well plate. Enzyme labeled antibody can be mixed with sample and applied to the plate. Uncaptured labeled antibody is then washed off the surface. After substrate is added the color development is observed. In this example, there is an inverse relationship between the color intensity and the amount of antigen present.

ELISA plates can include wells for detection of specific nitrofurans and/or metabolites, protein bound or otherwise. Multiple wells can be used to detect a variety of nitrofurans and/or metabolites. Such wells can include antibodies generated using one or more of the immunogens and/or techniques described herein.

Another embodiment utilizes antibody produced in accordance with various embodiments in a lateral flow assay test device and method including those described in U.S. Pat. No. 6,319,466, issued Nov. 20, 2001, which is incorporated herein.

In a lateral flow test device, antibody described herein can bind to nitrofuran parent and/or metabolite from a sample to form an analyte-antibody complex. The method and device can utilize a membrane strip, such as a nitrocellulose strip. One example utilizes colloidal gold particles as a label bound to the antibody. The size of the particle can be adapted to the porosity of the membrane strip. The particles are preferably sufficiently small to be transported along the membrane by capillary action of a fluid sample. The number of particles present in the test strip may vary, depending on the size and composition of the test strip and the desired level of sensitivity of the assay. For example, using fewer particles may help increase test sensitivity.

Any one of a variety of labels may be employed including colloidal gold particles. Other useful labels include, but are not limited to, colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles, colloidal metal ferrite particles, any of the above-mentioned colloidal particles coated with an organic or inorganic layer; protein or peptide molecules; liposomes; or organic polymer latex particles, such as polystyrene latex beads. Still other labels may also be used including, but not limited to, luminescent labels; fluorescent labels; or chemical labels, such as electroactive agents (e.g., ferrocyanide); enzymes; radioactive labels; or radiofrequency labels.

The test device can include a support strip and a sample-absorbing matrix, for example composed of a cellulosic, sponge-like material. Such a sample absorbing matrix allows for absorbing an amount of the sample and can also filter unwanted substances from the sample prior to the sample contacting test reagents. The test device also can include a mobile-phase support attached to the support strip and in contact with the sample-absorbing matrix. In an example, a mobile-phase composition is disposed within or on the mobile phase support and has one or more labeled receptors, such as one or more gold labeled antibodies with affinity to a nitrofuran and/or metabolite thereof. These kits may also include various combinations of polyclonal and monoclonal antibodies.

The mobile-phase composition can be applied prior to test operation, for example by spraying and drying onto a porous surface such as polyethylene membrane. A useful membrane is POREX® (POREX is a registered trademark of Porex Technologies Corp. of Fairburn, Ga.) membrane. When exposed to a sample, for example of fluid milk, honey extract, shrimp extract or other liquid or liquefied matrix, the mobile phase composition can be carried in the sample flow together with the sample. In test operation the sample flows and the antibody binds to nitrofuran and/or metabolite present in the sample to form antibody-analyte complexes. Alternatively, the mobile phase can be combined with sample prior to application to the test strip or other solid support. In this alternative embodiment antibody can bind to nitrofuran and/or metabolite present in the sample prior to contact with the test strip.

In an example, the test strip includes a stationary-phase support strip, which may be part of the same strip as the mobile-phase composition, or on a separate strip in fluid flow contact with the first strip. The support strip has a first membrane end in contact with the mobile-phase composition and a second membrane end that may be in contact with an optional disposal zone. Lateral-capillary flow of the sample is from the first membrane end to the second membrane end.

The one or more test zones may include a binder, such as a representative analyte or analogue thereof, which capture unbound labeled receptor. One or more optional control zones may also be on the stationary-phase membrane. The control zone may contain receptor for the analyte receptor, for example, antibody to the particular receptor, such as anti-species antibody, for binding with both analyte-bound receptor and excess unbound receptor. Alternatively, the control zone may be involved in an independent reaction that informs the user that the test is complete and includes consistent visual indicators, such as color development, for comparison to the test zone. The control zone may can generate signal either on contact with sample or on contact with specific test material, such as labeled receptor, such as when the control zone includes an anti-species antibody or one of the several useful antibody binders known in the art including protein A, protein G or recombinant varieties of proteins A and G.

Examples of possible test zone binders include nitrofurans, nitrofuran metabolites, acrylonitrile derivatives of a nitrofuran, or analogues thereof. For example nitrofurantoin metabolite (NFTM)-Cys-adduct, nitrofurazone (NFZM)-Cys adduct, furazolidone (FZDM)-Cys adduct, furaltadone (FTDM)-Cys adduct, either synthetically derived or the related naturally occurring species. Such a binder may be disposed on the test zone portion of the membrane for example by spraying. Prior to spraying, said binder can be conjugated to an attachment or carrier protein. Suitable attachment proteins are known to those skilled in the art to be proteins that bind readily to solid supports, such supports that include nitrocellulose. A useful attachment protein includes a carrier protein, i.e., a protein commonly used in conjunction with an immunogen, such as generally water soluble proteins with multiple accessible amino groups including albumin, e.g., bovine serum albumin (BSA), ovalbumin (OVA), keyhole limpet hemocyanin (KLH) and thyroglobulin (THG).

The lateral flow test device and method can also be in a sandwich assay format or an inhibition/competitive format. Multiple test zones can be utilized, for example to detect the presence of multiple analytes using multiple specific antibodies. In such multiple analyte tests, multiple control lines may or may not be required.

An embodiment includes a lateral flow assay that is capable of rapidly detecting one or more nitrofurans and/or metabolites such as tissue bound metabolites of nitrofurans in a sample. Such lateral flow assay formats can include those described in U.S. Pat. Nos. 6,319,466; 6,475,805; 5,985,675; and U.S. patent application Ser. No. 09/961,988, the teachings of which U.S. patents and U.S. patent applications are incorporated herein by this reference.

Lateral flow test results can be interpreted visually or by use of a reader, or analyzer, such as a ROSA reader (ROSA is a registered trademark of Charm Sciences, Inc. Lawrence, Mass.). Other reader/analyzer examples include fluorometers, luminometers, bar code readers, radiation detectors (such as scintillation counters), UV detectors, infrared detectors, electrochemical detectors or optical readers, such as spectrophotometers. The reader can be used to distinguish between one or more test zones and one or more control zones or simply to determine a relative change in the test zone. In one embodiment the reader is a ROSA reader. In a particular embodiment, the analyzer is an optical reader, e.g., the reader described in U.S. Pat. No. 6,124,585, issued Sep. 26, 2000, hereby incorporated by reference.

In an embodiment not utilizing a lateral flow test strip, a radiolabeled tracer can be employed with the antibody. For example, in a method known as the Charm II method, an IGGSORB tablet (IGGSORB is a registered trademark of The Enzyme Center, Lawrence, Mass.) containing a lyophilized preparation of protein A fixed to the cell walls of inactivated Staphylococcus aureas, is added to a test tube along with 300 μL of deionized water. An appropriate amount of antibody is added to the tube and the tube is mixed. If required, an amount of buffer, for example 5 ml of MSU-EB (from Charm Sciences, Inc.) is added to the tube along with 5 μL of appropriate radiolabeled tracer and the tube is again mixed. The tube is incubated for five minutes at 40° C. and then centrifuged for 5 minutes at 3400 rpm. The supernatant is poured off, OPTIFLUOR scintillation fluid (PerkinElmer) is added to the tube and the tube is counted in a scintillation counter, for example a photomultiplier based system such as a Charm 6600 reader (Charm Sciences, Inc.).

In another embodiment prior to assaying, such as prior to performing a radioimmunoassay, the NF metabolite, whether or not protein bound, is separated from possible test interferences. Such interferences exist, for example, in dark honey samples. In an example, honey is diluted with pH 7.5 Tris/phosphate buffer and combined with an appropriate chromatographic media. Useful resins include strong anion exchange resins such as a High Q resin from BioRad. The mixture is centrifuged and the supernatant is used as the sample for the radioimmunoassay.

Another embodiment includes an N-linked NF metabolite conjugate of the following structure:

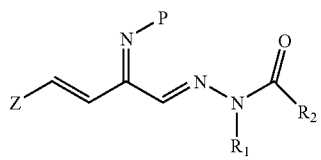

wherein P can be a peptide, protein, nucleic acid, polysaccharide or small molecular biochemical alone or covalently linked to a protein; wherein $R_1$ can be H or part of a heterocyclic ring structure such as a heterocyclic ring structure with an unsubstituted two-carbon chain, part of a heterocyclic ring structure of a two-carbon chain with an oxo (=O), 4-morpholinomethyl, or a 5 or 6 membered heterocyclicalkyl ring substitution; and wherein $R_2$ can be, for example, NH and O when enclosed in a heterocyclic ring said heterocyclic ring including $R_1$, or $NH_2$ when part of a linear side chain and wherein Z can be a functional group such as —CN, —OH, —O—CO2H, halides, carboxylate, —OR where R is an alkyl or acyl group of a low carbon chain and —NHR where R is an alkyl or acyl group of a low carbon chain.

For example, reaction of NF metabolites with beta-alanine at around pH 9 gives the following product:

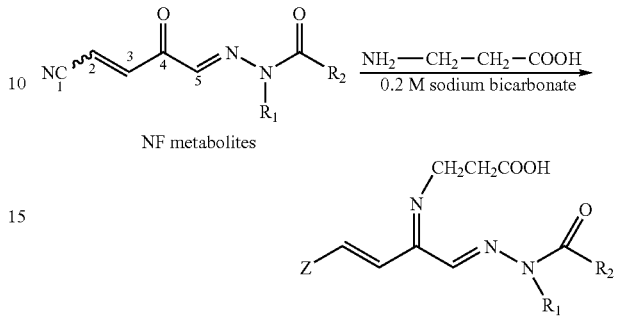

At elevated pH (e.g. pH 9), NF metabolites (including FZDM, FTDM, NFTM and NFZM) rapidly bind covalently to an amine containing molecule creating a linkage in the form of a Schiff base at the 4-keto position of the NF metabolites. The linkage results in the formation of a chromophore in the conjugate which absorbs light maximally at 365 nm. The amine containing molecules can be a small organic molecule such as b-alanine or N-acetyl-lysine or a protein molecule such as alpha-amylase or BSA. The absorbance at 365 nm can be used to quantify the nitrofuran metabolite moiety in the nitrofuran metabolite-protein conjugate for those proteins which absorb light in the UV region only.

NF metabolite protein conjugates of the present invention can be prepared, for example, by mixing NF metabolites in an organic solvent such as DMF with protein (e.g. BSA or alpha-amylase) at a selected molar ratio in a pH 9 buffer (e.g. borate buffer) to obtain the desired N-linked direct protein conjugates with the resulting incorporation ratio which can be adjusted based on the input molar ratio and reaction time. Purification of the protein conjugates can be through using a SEPHADEX sizing column to separate the NF metabolite protein conjugate from the unreacted NF metabolite, followed by a dialysis for completeness.

Protein conjugates of this embodiment, where P is a protein attached to the NF metabolite such as through a lysine side chain, forming the so-called N-linked direct conjugates, are useful as immunogens for raising antibodies against NF metabolites, (including derivatives or analogous molecules), test reagents, such as a binding partner of anti-NF metabolites immobilized on a solid phase such as ELISA, latex beads, and paramagnetic particles. The protein conjugate can also be useful as a protein-bound positive control standard of NF metabolites in binding assays. Protein conjugates of this embodiment also can also be used in the preparation/manufacture of the N-linked direct protein conjugates as compared to NF metabolites-Cys-protein conjugates (S-linked protein conjugates)

EXAMPLES

It should be noted that the names of nitrofuran metabolites, acrylonitrile and 4-oxo-pent-2-enenitrile nitrofuran derivatives may be referred to herein interchangeably. The systematic chemical nomenclatures of the individual nitrofuran metabolites are suggested in the following examples. For easy reference to the individual compounds, a 4-letter acronym system, abbreviated names and numbering were adopted and correlated to the chemical nomenclatures in parentheses in the following examples. For instance, the nitrofurantoin metabolite may be referred to as NFTM. The N-acetyl cysteine adduct of NFTM may be referred to as NFTM-Cys.

Example 1

Stepwise Synthesis of Nitrofurantoin Metabolite-N-Acetyl-L-Cysteine Adduct (NFTM-Cys, 5a)

Synthesis of 5-Azido-2-furaldehyde: The conversion of 5-nitro-2-furaldehyde to 5-azido-2-furaldehyde. A solution of 5-nitro-2-furaldehyde (2 g, 14.2 mmole) in 28 ml of DMSO was treated with sodium azide (0.92 g, 14.2 mmole) in small portions with stirring over 1.5 hr. The temperature of the reaction mix was maintained at about 20° C. in a water bath. The reaction was monitored by silica gel thin layer chromatography (TLC) two hours after the azide addition and found to be complete. The reaction mix was poured slowly to 200 ml of ice water in a beaker and extracted with chloroform (3×50 ml) in a separating funnel. The combined organic extracts were washed with brine, dried over sodium sulfate, filtered and evaporated to give a brown solid (1.27 g, 9.27 mmole, 65% yield). TLC analysis showed a homogeneous single spot with Rf value of about 0.75 when developed with ethyl acetate:petroleum ether (1:1). The compound was directly used for the preparation of acrylonitrile derivatives without further purification.

Synthesis of 5-(2,4-Dioxoimidazolidin-1-ylimino)-4-oxo-pent-2-enenitrile (nitrofurantoin metabolite, NFTM 1): A solution of 5-azido-2-furaldehyde (240 mg, 1.75 millimole (mmole)) in 20 milliliters (ml) of ethanol was added dropwise over 10-20 minutes to a solution of 1-aminohydantoin hydrochloride (320 mg, 2.1 mmole) in 25 ml of ethanol:water (4:1) and the mixture was chilled in an ice bath. The reaction mixture turned into a yellow-orange suspension within thirty minutes and was gradually heated to about 60° C. to form a complete solution. The heating continued for another 24 hours after which time it was allowed to cool and evaporated to dryness. The dark residue was triturated with 4-5 portions (15 ml each) of acetonitrile to obtain a suspension which was then filtered through a filter paper. The filtrate was evaporated to dryness. The residue was dissolved in 3 ml of acetone and streaked on two preparative silica gel TLC plates (EM Science, Cat # 5717-7) and developed with ethyl acetate: petroleum ether (3:1). The fast moving major band (Rf around 0.51) detected under UV light was stripped, and the silica gel was ground to a fine powder and eluted with acetone. The acetone eluent was evaporated to give a pale yellow solid which showed a homogeneous single spot on TLC (137 mg, 0.67 mmole, 38% yield). Alternatively the crude reaction product can be purified by silica gel column chromatography and further recrystallized from 30% ethyl acetate/hexanes to give the pure desired product (mp 171-173° C.). Elemental analysis supported a molecular formula of $C_8H_6N_4O_3$. 0.15 EtOAc. The structure of compound 1 was established by $^1$H and $^{13}$C NMR analysis as shown in FIGS. 1-4. $^1$H NMR analysis of 1 revealed that the acrylonitrile moiety has a trans (E)-configuration (coupling constant J=16.5 Hz). MALDI-TOF mass spectral analysis confirmed structure 1 with the M+1 peak of 207.22

Synthesis of S-{3-[5-(2,4-Dioxoimidazolidin-1-ylimino)-4-oxo-pentanenitrile]}-N-acetyl-L-cysteine (nitrofurantoin metabolite-N-acetyl-L-cysteine adduct, NFTM-Cys 5a): A solution of N-acetyl-L-cysteine (77 mg, 0.470 mmole) in 10 ml of water:acetonitrile (3:2) was added dropwise to a solution of NFTM (compound 1, 100 mg, 0.485 mmole) in 20 ml of acetonitrile. The reaction mixture was stirred at room temperature for about 3 hours and evaporated to complete dryness under a high vacuum. Silica gel TLC analysis carried out with the use of two separate solvent systems (a) ethyl acetate: petroleum ether (1:1) and (b) chloroform:methanol:water (73:24:3) showed that compound 1 was mostly consumed and the adduct 5a formation was essentially clean and complete. Because of the much higher polarity of the adduct, its presence can be easily distinguished from the starting compound 1. MALDI-TOF mass spectral analysis confirmed the molecular weight of the adduct based on the M+1 peak of 370.31.

The absolute configuration of the newly generated asymmetric center at C-3 position of the pentanenitrile moiety was a mixture of (R) and (S) configurations based on the $^1$H NMR chemical shifts pattern. The adduct 5a thus prepared was used without further purification for the protein conjugate preparation as described in Example 6 below.

Example 2

Stepwise Synthesis of Nitrofurazone Metabolite-N-Acetyl-L-Cysteine Adduct (NFZM-Cys, 6a)

Synthesis of 5-(N-Ureidoimino)-4-oxo-pent-2-enenitrile (nitrofurazone metabolite NFZM, 2): A solution of 5-azido-2-furaldehyde (92 mg, 0.67 mmole) in 4 ml of ethanol was added dropwise to a solution of semicarbazide hydrochloride (75 mg, 0.67 mmole) in 10 ml of ethanol:water (5:1) mixture. The reaction mix was stirred at room temperature overnight and evaporated to dryness. The residue was dissolved in 1.2 ml of acetone and streaked on one preparative silica gel TLC plates (EM-5717-7), developed with ethyl acetate:petroleum ether (9:1). Two well-separated major bands (upper band with Rf of 0.56 and lower band with Rf of 0.20) were detected under UV lights and were separately stripped and eluted with excess of ethyl acetate. The ethyl acetate eluents were evaporated to give pale yellow residues (45 mg and 35 mg, respectively). On silica gel TLC, both residues showed identical pattern of two distinctly separated spots with Rf of 0.56 and 0.33 when the TLC was developed with ethyl acetate:petroleum ether (6:1). The TLC analysis suggested that both residues contained interconvertible cis and trans isomers and were, therefore, combined (total yield 0.48, 72%). $^1$H NMR analysis of 2 confirmed that it is a mixture of two isomers with the acrylonitrile moiety in cis (Z) and trans (E)-configurations (coupling constant J=11.6 and 16.5 Hz, respectively).

Synthesis of S-{3-[5-(N-Ureidoimino)-4-oxo-pentanenitrile]}-N-acetyl-L-cysteine (nitrofurazone metabolite-N-acetyl-L-cysteine adduct NFZM-Cys, 6a): A solution of N-acetyl-L-cysteine (60 mg, 0.370 mmole) in 4 ml of water: acetonitrile (3:2) was mixed with a solution of NFMZM (compound 2, 64 mg, 0.385 mmole) in 6 ml of acetonitrile: DMF (2:1). The reaction mixture was stirred at room temperature overnight and evaporated to complete dryness under high vacuum. Silica gel TLC analysis carried out with the use of two separate solvent systems (a) ethyl acetate: petroleum ether (6:1) and (b) chloroform:methanol:water (73:24:3) showed that compound 2 was mostly consumed and the adduct 6a formation was essentially clean and complete. Similar to adduct 5a, because of the much higher polarity of the adduct, its presence can be easily distinguished from the starting compound 2. MALDI-TOF mass spectral analysis confirmed the molecular weight of the adduct with M+1 peak of 330.65 and its sodiated peak of 352.60. The absolute configuration of the newly generated asymmetric center at C-3 position of the pentanenitrile moiety was a mixture of (R) and (S) configurations based on the NMR chemical shifts pattern. The adduct 6a thus prepared was used without further purification for the protein conjugate preparation as described in Example 6 below.

Example 3

Stepwise Synthesis of Furazolidone Metabolite-N-Acetyl-L-Cysteine Adduct (FZDM-Cys, 7a)

Synthesis of 5-(2-oxo-oxazolidin-3-ylimino)-4-oxo-pent-2-enenitrile (Furazolidone metabolite, FZDM, 3): A solution of 5-azido-2-furaldehyde (84 mg, 0.61 mmole) in 3 ml of ethanol was added dropwise to a solution of 3-amino-2-oxazolidone (Sigma, 56 mg, 0.55 mmole) in 5 ml of ethanol:water (5:1) mixture, followed by 2 ml of 1N HCl. The reaction mix was stirred at room temperature for 24 hours and evaporated to dryness. The residue was triturated with 20 ml of ethyl acetate:chloroform (4:1), filtered through a medium porosity frit to give a light brown solid (70 mg, 0.36 mmole, 66% yield). Silica gel TLC analysis showed a homogeneous single spot with Rf of 0.6 when developed in ethyl acetate. $^1$H NMR analysis of 3 revealed that the acrylonitrile moiety has cis (Z) configurations (coupling constant J=11.6 Hz).

Synthesis of S-{3-[5-(2-oxo-oxazolidin-3-ylimino)-4-oxo-pentanenitrile]}-N-acetyl-L-cysteine (furazolidone metabolite-N-acetyl-L-cysteine adduct, FZDM-Cys, 7a): A solution of N-acetyl-L-cysteine (52 mg, 0.32 mmole) in 3 ml of water:acetonitrile (3:2) was added dropwise to a solution of FZDM (compound 3, 68 mg, 0.35 mmole) in 9 ml of acetonitrile. The reaction mixture was stirred at room temperature overnight and evaporated to complete dryness under high vacuum. Silica gel TLC analysis carried out with the use of two separate solvent systems (a) ethyl acetate and (b) chloroform:methanol:water (55:40:5) showed that compound 3 was mostly consumed and the adduct 7a formation was essentially clean and complete. MALDI-TOF mass spectral analysis confirmed the molecular weight of the adduct based on the peaks of 356.64 and M+1 peak of 357.66. The absolute configuration of the newly generated asymmetric center at C-3 position of the pentanenitrile moiety was a mixture of (R) and (S) configurations based on the NMR chemical shifts pattern. The adduct 7a thus prepared was used without further purification for the protein conjugate preparation as described in Example 6 below.

Example 4

Stepwise synthesis of Furaltadone Metabolite-N-Acetyl-L-Cysteine Adduct (FTDM-Cys, 8a)

Synthesis of 5-(5-Morpholinomethyl-2-oxo-oxazolidin-3-ylimino)-4-oxo-pent-2-enenitrile (Furaltadone metabolite, FTDM, 4): A solution of 5-azido-2-furaldehyde (33 mg, 0.24 mmole) in 2 ml of ethanol was added dropwise to a solution of 5-morpholinomethyl-3-amino-2-oxazolidone (Sigma, 43 mg, 0.21 mmole) in 2.5 ml of ethanol:water (5:1) mixture, followed by 0.5 ml of 1N HCl. The reaction mix was stirred at room temperature overnight and evaporated to dryness. The residue was partitioned between 20 ml of ethyl acetate and 10 ml of 2% sodium bicarbonate. The ethyl acetate layer was kept and the aqueous layer extracted with 2×15 ml of ethyl acetate. The combined organic layer was dried over sodium sulfate, filtered and evaporated to dryness. (51 mg, 0.17 mmole, 83% yield). Silica gel TLC analysis showed a homogeneous single spot with Rf of 0.44 when developed in ethyl acetate. $^1$H NMR analysis of 4 revealed that it is a mixture of two isomers with the acrylonitrile moiety in cis (Z) and trans (E)-configurations (coupling constant J=11.6 and 16.5 Hz, respectively).

Synthesis of S-{3-[5-(5-Morpholinomethyl-2-oxo-oxazolidin-3-ylimino)-4-oxo-pentanenitrile]}-N-acetyl-L-cysteine (furaltadone metabolite-N-acetyl-L-cysteine adduct, FTDM-Cys 8a): A solution of N-acetyl-L-cysteine (22 mg, 0.137 mmole) in 1.5 ml of water:acetonitrile (3:2) mixture was added dropwise to a solution of FTDM (compound 4, 42 mg, 0.143 mmole) in 6 ml of acetonitrile. The reaction mixture was stirred at room temperature overnight and evaporated to complete dryness under high vacuum. Silica gel TLC analysis in chloroform:methanol:water (73:24:3) system showed that compound 4 was mostly consumed and the adduct 8 formation was essentially clean and complete. MALDI-TOF mass spectral analysis confirmed the molecular weight of the adduct with the M+1 peak of 457.01 and its sodiated peak of 479.01. The absolute configuration of the newly generated asymmetric center at C-3 position of the pentanenitrile moiety was a mixture of (R) and (S) configurations based on the NMR chemical shifts pattern. The adduct 8a thus prepared was used without further purification for the protein conjugate preparation as described in Example 6 below.

Example 5

A Representative Stepwise Synthesis of Furazolidone Metabolite-N-Acetyl-Glutathione Adduct (FZDM-Glut, 7b)

Synthesis of N-Acetyl-glutathione: A solution of glutathione (1 g, 3.25 mmole) in 10 ml of water was added over 1 hr to a mixture of acetic anhydride (10 ml) and acetic acid (10 ml) at room temperature. After the addition was complete, the reaction mixture was chilled on ice. Additional acetic anhydride (5 ml) was added and the reaction mix was stirred while it gradually warmed to room temperature overnight. The reaction mixture was treated with 300 ml of ethyl ether and cooled overnight to obtain crystallized product. A white solid was obtained by filtering the reaction mix, and washing with more ether. More crystallized product was generated in the filtrate. The filtration and washing were repeated a second time and the white solids were combined and air-dried (585 mg, yield 51.5%).

Synthesis of S-{3-[5-(2-oxo-oxazolidin-3-ylimino)-4-oxo-pentanenitrile]}-N-acetyl-glutathione (furazolidone metabolite-N-acetyl-glutathion adduct FZDM-Glut 7b): A solution of N-acetyl-glutathone (111 mg, 0.31 mmole) in 5.5 ml of water:acetonitrile (3:2) was added dropwise to a solution of FZDM (compound 3, 56 mg, 0.29 mmole) in 11 ml of acetonitrile. The reaction mixture was stirred at room temperature overnight and evaporated to complete dryness under high vacuum. Silica gel TLC analysis carried out with the use of two separate solvent systems (a) ethyl acetate and (b) chloroform:methanol:water (55:40:5) showed that the formation of the glutathione adduct was significantly slower in comparison to the corresponding cysteine adduct. Compound 3 was only about one third consumed after half an hour of mixing and the reaction had to go overnight to form mostly the desired adduct. The adduct 7b thus prepared was used without further purification for the protein conjugate preparation as described below.

Example 6

Preparation of NF Metabolites-Cys Adducts Protein Conjugates

The example provides a general method of conjugating NF metabolites-cys adducts (compounds 5a, 6a, 7a and 8a; 5b, 6b, 7b and 8b) to protein carriers including cationized BSA (cBSA), KLH, thyroglobulin (THG) and ovalbumin. The procedure includes stepwise adduct activation, protein coupling reactions, column sizing (SEPHADEX G-25 Fine of Pharmacia, now Amersham Biosciences) purification, dialysis of the protein conjugate fractions and protein concentration analysis. Where possible, the molecular weight of the protein conjugates were determined by MALDI-TOF mass spectrophotometry.

Activation: In the activation step, the molar ratio between the adducts and the coupling reagents, DCC (1,3-dicyclohexylcarbodiimide) and NHS (N-hydroxysuccinimide) was chosen preferably in 1:1.7-2.2:1.1-1.2, respectively. DMF (N,N-dimethylformamide) anhydrous was the preferred solvent. All the reactants were stored in a dessicator before use or pre-dried thoroughly in a vacuum oven or by prolonged rota-evaporation to ensure dryness. The activation reaction was set up in an ice bath by adding DCC and NHS in DMF solution sequentially to the adduct also in DMF solution. The total volume of DMF should be maintained preferably not to exceed 20% (v/v), preferably around 10%, of the solvent mix (DMF plus buffer) used in the next coupling reaction. The reaction was allowed to proceed from several hours to overnight, optionally treated with equimolar of glacial acetic acid to scavenge the excess of DCC for at least another hour, then filtered to remove the DCU (dicyclohexyl urea) reaction by-product. The filtrate was used directly for protein coupling.

Coupling: In the protein coupling step, BSA that has been derivatized with ethylene diamines (cationized BSA or SuperCarrier Immuno Modulator from Pierce Biotech) was preferred over regular BSA. The molecular weight of cationized BSA was estimated to be in the range of 67,000-69,000. The average of 68,000 was used for molar calculation. For the coupling reaction, the molar input ratio of NF metabolites-cys adducts to cationized BSA can be chosen between 30:1 to 150:1, preferably 60-90:1. For KLH (from Pierce Biotech), because of the high heterogeneity of the protein, a very rough estimate of the molecular weight of 5,000,000 was used for molar calculation. Generally it is adequate to use the molar input ratio of 500:1 to 3,000:1. For thyroglobulin (MW 670, 000, purchased from Sigma), the range of molar ratio between 500-1500:1, preferably 1000:1 was chosen. For the ovalbumin (MW 43,000-45,000) conjugates the molar input ratio between 20-60:1 were chosen. The coupling reactions can be carried out in 0.02 to 0.2 M PBS with or without saline at pH 7.0-8.5, preferably 7.2-8.0. The protein concentrations can range from 2-10 mg/ml, preferably 4-8 mg/ml. The coupling reaction was allowed to proceed for several hours to overnight at room temperature with gentle shaking.

Sizing purification. The coupling reaction mixture normally shows some level of turbidity, or minor precipitate, which can be removed by filtration or centrifugation followed by removal of the supernatant. The supernatant can then be equilibrated with phosphate buffer, pH 7.2-7.4 and purified through a SEPHADEX (SEPHADEX is a registered trademark of GE Healthcare Bio-Sciences AB LTD Liability CO SWEDEN) G-25 fine column. Alternatively, the supernatant can be can be cleaned by dialyzing using dialysis tubing with molecular weight cut off of 12, 400 equilibrated with phosphate buffer, pH 7.2-7.4

Mass determination: Protein conjugates with masses estimated to be less than 200 KDa was submitted externally for MALDI-TOF mass spectral analysis. Samples were desalted prior to submission. Results were reported as the average of the molecular ion peak clusters from at least 3 separate determinations.

Example 7

A Representative Preparation of NFTM-Cys-cBSA Conjugate (9a)

A solution of NFTM-Cys (compound 5a, 5.5 mg, 15 umole) in 0.4 ml of DMF was chilled in an ice bath, treated with a solution of DCC (6.8 mg, 33 umole) in 0.4 ml of DMF for 10 minutes, followed by a solution of NHS (2 mg, 18 umole) in 0.2 ml of DMF. The reaction mixture was stirred at room temperature overnight in a brown vial, treated with glacial acetic acid (3 µl) in 10 µl of DMF for a few hours and filtered through glass wool to obtain filtrate which was added directly to a cBSA (20 mg, 0.3 umole) solution in 4 ml of 20 mM phosphate, pH 7.2. The conjugation reaction was shaken at room temperature overnight, filtered through glass wool, purified through SEPHADEX G-25 fine column, dialyzed against 1 liter of 20 mM phosphate, pH 7.2, and quantified as described above. MALDI-TOF mass spectral analysis showed the NFTM-Cys-cBSA conjugate had an average molecular weight of 75,137 amu, an increase of about 7,000 mass unit, corresponding to the attachment of about 19 molecules of NFTM-Cys to cBSA.

Example 8

A Representative Preparation of FZDM-Glut-THG Conjugate (10c)

A solution of FZDM-Glut (compound 7b, 81.2 mg, 150 umole) in 0.9 ml of DMF was chilled in an ice bath, treated with a solution of DCC (52.5 mg, 255 umole) in 0.3 ml of DMF for 10 minutes, followed by a solution of NHS (20.7 mg, 180 umole) in 0.3 ml of DMF. The reaction mixture was stirred at room temperature overnight in a brown vial, treated with glacial acetic acid (9 µl) for one hour and filtered through glass wool to obtain filtrate which was added directly to a thyroglobulin (100 mg, 0.15 µmole) solution in 20 ml of 0.1 M phosphate, pH 8.0. The conjugation reaction was shaken at room temperature for 7 hrs, refrigerated overnight, filtered through glass wool, purified through SEPHADEX G-25 fine column, dialyzed against 1 liter of 20 mM phosphate, pH 7.2, and quantified as described above.

Example 9

Preparation of N-Linked NFTM-Beta-Ala (11a)

A solution of NFTM (compound 1, 3.7 mg, 18 umole) in 0.25 ml of acetonitrile was treated with a solution of beta-alanine (5.4 mg, 61 umole) in 1.0 ml of 0.2 M NaHCO$_3$. The reaction mixture was stirred at room temperature for 5 hours and evaporated under vacuum. Silica gel TLC analyses in (a) ethyl acetate and (b) chloroform:methanol:water (20:92:8) system was carried out to monitor the completion of the reaction. The development with ethyl acetate allowed the view of the consumption of less polar NFTM under UV light. The more polar solvent system (b) was employed to view the generation of polar NFTM-beta-Ala adduct. The crude product was taken up with 400 µl of water:methanol:acetonitrile (2:1:1) and purified on a silica gel 60F TLC plate (EM Science, Cat # 5715-7, 20×20 cm), developed with the same chloroform:methanol:water (20:92:8) solvent system. The major UV band at around Rf of 0.60 was stripped and eluted with same solvent system. The eluted product solution was evaporated (3.5 mg, 66% yield).

Example 10

Preparation of N-Linked NFTM-cBSA Conjugate (12a)

A solution of NFTM (compound 1, 4.0 mg, 18 umole) in 0.4 ml of DMF was added dropwise to a solution of cBSA (20 mg, 0.3 umole) in 4 ml of 0.1 mM phosphate, pH 7.4. The conjugation reaction was shaken gently at room temperature overnight, purified, dialyzed and assayed as described in example 6. MALDI-TOF mass spectral analysis showed the N-linked NFTM-cBSA conjugate had an average molecular weight of 70,992 amu, an increase of about 3,000 mass unit, corresponding to the attachment of about 14.6 molecules of NFTM to cBSA.

Example 11

Enzymatically Derived Immunogens

Diaphorase (SIGMA D-5540, EC 1.8.1.4) was reacted with a nitrofuran parent compound to facilitate the attachment of the enzymatically-reduced parent compound to a protein.

Preparation of protein/FMN/β-NADH/Diaphorase mixture: In a 15-ml conical tube, a solution of KLH in water (Pierce, 100 mg/ml) or a suspension of Bti (deactivated *Bacillus thuringiensis israelensis* toxin 100 mg/ml) also in water was mixed with a solution of FMN (Riboflavin 5'-Phosphate, 40 mg, Sigma R-7774) and B-NADH (40 mg) in 6 ml of 200 mM NaPhos, 0.8M NaCl, pH 8.5. Diaphorase (100 units, 20 mg by weight) was reconstituted with 900 µl of water separately, and added to the protein/FMN/β-NADH solution.

Preparation of nitrofuran solutions: Nitrofuran parent compounds (nitrofurantoin, nitrofurazon, and furaltadone) were separately dissolved at 40 mg/ml using DMF (N,N-Dimethylformamide, Aldrich 27,054-7) while furazolidone was dissolved at 0.3 mg/ml in water.

Enzymatic reduction and conjugation of nitrofurans to proteins: The reduction of the nitrofuran compounds and subsequent conjugation to the proteins were initiated by adding 125 µl of the individual nitrofuran/DMF mixture to each of the corresponding protein/FMN/β-NADH/Diaphorase mixture in the conical tubes. For the reactions of furazolidone protein/FMN/β-NADH/Diaphorase mixtures were transferred to a 50-ml conical tube and 30 ml of the furazolidone aqueous solution was added. These reactions (two for each nitrofuran compound: one KLH conjugation and one Bti conjugation) were incubated overnight at 37° C. The next day the KLH reactions were desalted using a Biorad Econopak Desalting column against 0.9M NaCl, 20 mM Sodium Phosphate buffer at pH 7.2. The Bti reactions were dialyzed against 20 mM Sodium Phosphate buffer at pH 7.2. The resulting conjugates were then labeled as follows:

Furazolidone—KLH (FZDM-KLH)

Furaltadone—KLH (FTDM-KLH)

Nitrofurantoin—KLH (NFTM-KLH)

Nitrofurazone—KLH (NFZM-KLH)

Furazolidone—Bti (FZDM-Bti)

Furaltadone—Bti (FTDM-Bti)

Nitrofurantoin—Bti (NFTM-Bti)

Nitrofurazone—Bti (NFZM-Bti)

The KLH conjugates were quantified using the Bradford protein determination method. The Bti conjugates were quantified using the Lowry protein determination method. After protein content determination, the conjugates were diluted to a concentration of 1 mg/mL. The KLH immunogens were stored frozen. The Bti immunogens were freeze-dried and stored in 5 mg/bottle.

Each of the 8 immunogens described above were injected into rabbits.

Example 12

Antibody Screening

Results in the following tables were generated using an ELISA assay. Within the well of each plate was dried 5 micrograms of target metabolite-cysteine-BSA (tables 1-4) or metabolite-glutathione-BSA (tables 5-9) at a ratio of metabolite-cysteine to BSA or metabolite-glutathione to BSA of (60:1). A 50 µl sample (buffer) was added to each well along with 50 µl of antibody solution. The mixture was mixed on a plate shaker for 10 minutes at room temperature. The well was then washed with a solution of 0.01% TWEEN-20 (Sigma) in phosphate buffer saline (Washing Solution). Phosphate buffered saline (PBS) is a solution of 137 mM NaCl, 3 mM KCl, 10 mM $Na_2HPO_4$, 2 mM $KH_2PO_4$. Next, 100 µl goat-anti-rabbit horseradish peroxidase (GAR-HRP) conjugate (1:1000 dilution) was added to the bottom of each well and mixed on a plate shaker for 10 minutes at room temperature. The well was then washed again with washing solution. 100 µl of 3,3',5,5'-tetramethylbenzidine (TMB) substrate was added to each well. The plate was covered with plate sealing tape and shaken form 5 minutes at room temperature. 100 µL of stopping solution (2M $H_3PO_4$) was then added to each well and the absorbance measured at 450 nm after 5 minutes or longer.

Some of the data below is referred to as unblanked, or raw, data while other data is blanked. By blanked well optical density OD we mean OD from the well after the background OD has been deducted. By background OD we mean the OD from wells treated with Secondary Ab (GabR-HRP) 1:1000 without sample. Deducting background OD accounts for non-specific binding in the assay. Unless otherwise noted, data presented is blanked data.

Results for percentage inhibition compare negative to positive results at particular ppb levels. For example, a negative result may give an OD of 1.237 while a positive result gives an OD of 0.702. The percent inhibition of antibody binding to the ELISA well, as reflected by that reduction in OD, is 43%.

Table 1

The following Table 1 results compares the sera from rabbit #3220 immunized with FZDM-Glut-THG conjugate (Example 8) with rabbit #2998 immunized with the enzymatically derived immunogen FZD-Bti (Example 11). Detection level tested was 2 parts per billion (2 ppb) of furazolidone.

Columns 1 and 2 include data from rabbit number 3220 from which the serum was diluted 1/1000. Column 1 shows negative sample results and column 2 shows results at 2 ppb. Columns 3 and 4 include data from rabbit number 2998 from which the serum was diluted 1/500. Column 3 shows negative sample results and column 4 shows results at 2 ppb.

TABLE 1

|  | 3220, 1/1000 | | 2998, 1/500 | |
| --- | --- | --- | --- | --- |
|  | Neg | 2 ppb | Neg | 2 ppb |
|  | 2.367 | 1.049 | 1.604 | 1.358 |
|  | 2.462 | 0.941 | 1.491 | 1.371 |
|  | 2.011 | 0.928 | 1.624 | 1.299 |
|  | 1.688 | 0.747 | 1.639 | 1.454 |
|  | 1.7 | 0.806 | 1.552 | 1.393 |
|  | 1.706 | 0.856 | 1.677 | 1.402 |
|  | 1.675 | 0.891 | 1.691 | 1.359 |
| Average | 1.944 | 0.888 | 1.611 | 1.377 |
| % inhibition |  | 54% |  | 15% |

Table 2

The following Table 2 results compare the sera from rabbit #3220 immunized with FZDM-Glut-THG conjugate with the sera from rabbit # 2998 immunized with the enzymatically derived immunogen FZDM-Bti.

Columns 1 and 2 include data from rabbit number 3220 from which the serum was diluted 1/1000. Column 1 shows negative results and column 2 shows results at 10 ppb. Columns 3 and 4 include data from rabbit number 2998 from which the serum was diluted 1/500. Column 3 shows negative results and column 4 shows results at 10 ppb.

TABLE 2

|  | 3220, 1/1000 | | 2998, 1/500 | |
| --- | --- | --- | --- | --- |
|  | Neg | 10 ppb | Neg | 10 ppb |
|  | 2.135 | 0.867 | 1.266 | 0.825 |
|  | 2.032 | 0.812 | 1.532 | 0.943 |
|  | 2.186 | 0.787 | 1.334 | 0.879 |
|  | 1.972 | 0.695 | 1.269 | 0.92 |
|  | 2.419 | 0.681 | 1.528 | 0.947 |
|  | 1.945 | 0.686 | 1.282 | 0.961 |
|  | 1.86 | 0.71 | 1.209 | 0.988 |
| Average | 2.078 | 0.748 | 1.346 | 0.923 |
| % inhibition |  | 64% |  | 31% |

Table 3

The following results compare serum antibody binding of six different rabbits injected with the enzymatically derived FTDM-Bti immunogen produced as described in Example 11. The column heading pooled refers to serum pooled from previous rabbit bleeds and is used to compare the results from current rabbit bleeds. All data is unblanked raw data.

TABLE 3

|  | Pooled | 3311 | 3312 | 3313 | 3319 | 3320 | 3321 |
| --- | --- | --- | --- | --- | --- | --- | --- |
| Neg | 1.089 | 0.97 | 0.616 | 1.367 | 1.196 | 1.703 | 1.158 |
| " | 1.127 | 0.983 | 0.605 | 1.314 | 1.137 | 1.576 | 1.132 |
| " | 1.086 | 0.911 | 0.647 | 1.29 | 1.034 | 1.559 | 1.216 |
| " | 1.03 | 0.902 | 0.65 | 1.337 | 1.023 | 1.586 | 1.136 |
| average | 1.083 | 0.942 | 0.630 | 1.327 | 1.098 | 1.606 | 1.161 |
| Standard dev | 0.040 | 0.041 | 0.022 | 0.033 | 0.083 | 0.066 | 0.039 |
| % CV | 4% | 4% | 4% | 2% | 8% | 4% | 3% |
| 1 ppb | 0.664 | 0.457 | 0.55 | 0.477 | 0.736 | 1.012 | 0.865 |
| " | 0.58 | 0.499 | 0.548 | 0.51 | 0.783 | 0.959 | 0.924 |
| " | 0.642 | 0.562 | 0.582 | 0.533 | 0.779 | 0.984 | 0.861 |
| " | 0.584 | 0.464 | 0.509 | 0.49 | 0.837 | 1.059 | 0.943 |
| average | 0.602 | 0.508 | 0.546 | 0.511 | 0.800 | 1.001 | 0.909 |
| Standard dev | 0.035 | 0.050 | 0.037 | 0.022 | 0.032 | 0.052 | 0.043 |
| % CV | 6% | 10% | 7% | 4% | 4% | 5% | 5% |
| % Inhibition | 44% | 46% | 13% | 61% | 27% | 38% | 22% |

Table 4

The following results compare serum antibody binding of five different rabbits injected with the enzymatically derived NFTM-Bti immunogen produced as described in Example 11. Results are from fifth month rabbit serum samples. All serum was diluted 1:2000 prior to testing.

TABLE 4

|  | 2995 | 2994 | 2993 | 2992 | 2991 | Pooled Ab |
| --- | --- | --- | --- | --- | --- | --- |
| Neg | 1.316 | 1.025 | 3 | 1.328 |  | 1.628 |
| Neg | 1.271 | 1.033 | 3 | 1.321 | 2.889 | 1.429 |
| Neg | 1.202 | 1.026 | 3 | 1.328 | 2.764 | 1.336 |
| Neg | 1.226 | 1.012 | 3 | 1.291 | 2.647 | 1.265 |
| Neg | 1.193 | 1.031 | 3 | 1.241 | 2.562 | 1.304 |
| Neg | 1.195 | 1.032 | 3 | 1.297 | 2.582 | 1.287 |
| Neg | 1.259 | 1.012 | 3 | 1.258 | 2.548 | 1.35 |
| Average | 1.237 | 1.024 | 3.000 | 1.295 | 2.665 | 1.371 |
| Standard dev | 0.046 | 0.009 | 0.000 | 0.035 | 0.135 | 0.125 |
| % CV | 4% | 1% | 0% | 3% | 5% | 9% |
| 1 ppb | 0.715 | 0.187 | 1.367 | 0.442 | 1.376 | 0.49 |
| 1 ppb | 0.729 | 0.189 | 1.329 | 0.385 | 1.22 | 0.451 |
| 1 ppb | 0.725 | 0.187 | 1.353 | 0.409 | 1.234 | 0.44 |
| 1 ppb | 0.672 | 0.184 | 1.235 | 0.398 | 1.148 | 0.417 |
| 1 ppb | 0.733 | 0.188 | 1.36 | 0.417 | 1.142 | 0.41 |
| 1 ppb | 0.669 | 0.189 | 1.233 | 0.391 | 1.171 | 0.419 |
| 1 ppb | 0.668 | 0.205 | 1.183 | 0.397 | 1.188 | 0.446 |
| Average | 0.702 | 0.190 | 1.294 | 0.406 | 1.211 | 0.439 |
| Standard dev | 0.030 | 0.007 | 0.075 | 0.019 | 0.080 | 0.027 |
| % CV | 4% | 4% | 6% | 5% | 7% | 6% |
| % Inhibition | 43% | 81% | 57% | 69% | 55% | 68% |

Table 5

The following results compare serum antibody binding of four different rabbits injected with the enzymatically derived NFTM-KLH immunogen produced as described in Example 11. Table 5 reflects results from fifth month rabbit serum samples. All serum was diluted 1:2000 prior to testing.

TABLE 5

|  | 3314 | 3315 | 3316 | 3317 |
| --- | --- | --- | --- | --- |
| Neg | 2.376 | 0.738 | 2.381 | 0.949 |
| Neg | 2.503 | 0.735 | 2.236 | 0.98 |
| Neg | 2.333 | 0.728 | 2.147 | 0.889 |
| Neg | 2.209 | 0.752 | 2.142 | 0.853 |

TABLE 5-continued

|  | 3314 | 3315 | 3316 | 3317 |
|---|---|---|---|---|
| Neg | 2.454 | 0.754 | 2.166 | 0.854 |
| Neg | 2.258 | 0.759 | 2.196 | 0.894 |
| Neg | 2.501 | 0.744 | 2.094 | 0.871 |
| Average | 2.376 | 0.744 | 2.195 | 0.899 |
| Standard dev | 0.117 | 0.011 | 0.093 | 0.048 |
| % CV | 5% | 2% | 4% | 5% |
| 1 ppb | 0.501 | 0.27 | 0.623 | 0.334 |
| 1 ppb | 0.499 | 0.301 | 0.589 | 0.317 |
| 1 ppb | 0.499 | 0.285 | 0.595 | 0.321 |
| 1 ppb | 0.477 | 0.243 | 0.595 | 0.316 |
| 1 ppb | 0.482 | 0.262 | 0.6 | 0.37 |
| 1 ppb | 0.457 | 0.274 | 0.494 | 0.336 |
| 1 ppb | 0.477 | 0.238 | 0.494 | 0.294 |
| Average | 0.485 | 0.268 | 0.570 | 0.327 |
| Standard dev | 0.016 | 0.022 | 0.053 | 0.024 |
| % CV | 3% | 8% | 9% | 7% |
| % Inhibition | 80% | 64% | 74% | 64% |

Example 13

ELISA Plate for Detecting Nitrofuran and/or Metabolites in a Competitive Assay

Plate Coating: Appropriate conjugate solution (any one of NFTM-Cys-BSA, NFZM-Cys-BSA, FTDM-Cys-BSA, FZDM-Cys-BSA depending upon the corresponding anti-nitrofuran metabolite antibody to be added to the well) was diluted to 0.05 mg/ml using the room temperature ZEPTO-BIND buffer (Zeptometrix Corp., Buffalo, N.Y.). Into each well, 100 µl of the conjugate solution was pipetted. The plate was covered with plastic plate sealing tape and incubated overnight (minimum of 16 hours) at 4° C. The plastic plate sealing tape was removed the next day and the wells washed with washing solution (as described in Example 17). To each well was added 300 µl of blocking buffer (5% BSA, 5% Sucrose in 0.1M Sodium Bicarbonate buffer pH 9.5). The plate was covered with a new plastic plate sealing tape and incubated at 37° C. for 2 hours. The plastic plate sealing tape was then removed and the wells washed with washing solution. The plate was placed (not sealed with plastic sealing tape) into a low humidity 21° C. incubator and allowed to dry for 4 hours.

Simultaneous competitive assay: Sample (50 µl) and Ab solution (50 µl) were added to each well and incubated for 25 minutes at room temperature. The wells were washed with wash solution and 100 µl of goat-anti-rabbit-horseradish peroxidase antibody conjugate, diluted 1:1000 with PBS (PBS as described in Example 12) were added to the bottom of each well. The reaction mixture was incubated for 25 minutes at room temperature, washed with washing solution and added with 100 µl of TMB substrate. The plate was covered with plastic plate sealing tape and gently mixed on a plate shaker for 15 minutes. After mixing, 100 µl of stopping solution (2 M $H_3PO_4$) was added to each well and the absorbance at 450 nm measured.

Sequential competitive assay: Assay sample was first prepared by mixing rabbit serum and sample (1:1), on the vortex mixer, capped, and incubated at room temperature for 15 minutes. To the appropriate wells, 100 µl of each prepared sample was pipetted. The plate was covered with the plastic plate sealing tape and incubated for 2 hours at 37° C. The plastic plate sealing tape was then removed and the wells washed with washing solution. After washing, 100 µl of goat-anti-rabbit-horseradish peroxidase antibody conjugate, diluted 1:10,000 with PBS, was added to the bottom of each well, and the plate covered with a new plastic plate sealing tape, incubated at 37° C. for 1 hour. After incubation, the plastic plate sealing tape was removed and the wells washed with washing solution and added 200 µl of TMB substrate. The plate was covered with a new plastic plate sealing tape, mixed gently on a plate shaker for 15 minutes at room temperature and the absorbance at 650 nm measured.

Example 14

An AOZ ELISA competitive binding assay is shown below, where the N-linked direct conjugate of FZDM-BSA is used as a binding partner conjugate coated on the ELISA plate, and the N-linked direct conjugate of FZDM-alpha-amylase is used as the positive control of protein-bound FZDM in comparison with the FZDM positive control. The antibody used in the assay was raised against the prior art FZDM-Glut-Thyroglobulin immunogen. Assays were run in two different buffers comparing PEB (Protein Elution Buffer) vs. PBS (Phosphate buffer saline). The results showed varying dose-responses (% inhibition) corresponding to different input levels of the positive controls (FZDM-amylase as well as FZDM) ranging from 0.1 to 10 ppb.

Example 15

Radioimmunoassay to Detect FZD and AOZ Metabolite

Preparation of Equilibrated MACRO-PREP High Q

One liter of de-ionized water was combined with 38.0 g Tris-HCL and 273.5 g Tris-base and mixed until dissolved (approximately 1 hour). The pH was adjusted to pH 9.00±0.05 with 5M HCL or 5M NaOH. The mixture was brought to final volume of 5 liters with de-ionized water. One liter was mixed with MACRO-PREP (MACRO-PREP is a registered trademark of Bio-Rad Laboratories, Hercules, Calif.) High Q Support in the bottle (1 liter of liquid) by hand. While swirling the resin bottle contents were added to a 1 liter column. The column end plug was removed and the flow-through discarded. The column was drained and refilled with 0.5 M Tris (pH. 9.0) and the solution flowed through the column. After one column volume was processed the flow was discarded and 0.5M Tris pH 9.0 was added two more times for a total of 3 equilibration rinses.

Equilibrated resin was recovered by refilling the column with 0.5 M Tris, pH. 9.0 and allowing the buffer to drip from the column until the meniscus was at the mark made on the side of the column tube. The column drain frit was replaced and the column top secured.

The equilibrated resin was re-suspended by inverting the column tube back and forth until the resin was fully in suspension. The re-suspension was poured into a clean 1 L flask containing a stir bar. 167 ml (0.5 M Tris, pH. 9.0) was added to the column rinse out remaining fines and adjust the final volume to 1.167 L.

The resin was re-suspend by placing the flask on a stir plate and mixing for 15 minutes.

For use, 40 ml (±0.5 ml) was dispensed into a each 60 mL WHATMAN (WHATMAN is a registered trademark of Whatman Paper Limited, Kent, England) plastic bottle using a Watson-Marlow pump.

Assay 5 grams of honey were diluted with 6 mL of 20 mM, pH 7.5Tris/phosphate buffer. 4 mL of the diluted sample was combined with 400 microliters of equilibrated MACRO-PREP High Q ion exchange resin and rotated for 4 minutes at 10 rpm's. The supernatant was combined with an antibody to FZD/AOZ, mixed by vortexing and incubated for 7 minutes at 35 degrees C. A radiolabeled representative metabolite was added, the mixture was vortexed, incubated for 3 minutes at 35 degrees C. and centrifuged for 4 minutes at 3,300 rpm. The supernatant was discarded and the pellet reconstituted with 4 mL deionized water and vortexed. The supernatant was again poured off and the pellet reconstituted with 300 microliters deionized water. Optifluor was added (3 mL) and then the mixture vortexed and counted on the Charm 6600 scintillation counter.

TABLE 6

Results are readouts from Charm 6600 scintillation, counter.

| | 4 mL Sample/400 uL of Resin | | | | | 5 mL Sample/400 uL of Resin | | | |
|---|---|---|---|---|---|---|---|---|---|
| | Neg Mix | 0.3 ppb (incurred) | 1.0 ppb (incurred) | Dark | | Neg Mix | 0.3 ppb (incurred) | 1.0 ppb (incurred) | Dark |
| | 986 | 610 | 360 | 914 | | 930 | 403 | 269 | 699 |
| | 1000 | 541 | 301 | 888 | | 755 | 428 | 276 | 732 |
| | 862 | 499 | 339 | 948 | | 813 | 469 | 225 | 693 |
| Avg = | 949 | 550 | 333 | 917 | Avg = | 833 | 433 | 257 | 708 |
| CV = | 8.0% | 10.2% | 9.0% | 3.3% | CV = | 10.7% | 7.7% | 10.8% | 3.0% |
| B/Bo = | | 0.58 | 0.35 | 0.97 | B/Bo = | | 0.52 | 0.31 | 0.85 |

| | 4 mL of Sample/700 uL of Resin | | | | | 5 mL of Sample/700 uL of Resin | | | |
|---|---|---|---|---|---|---|---|---|---|
| | Neg Mix | 0.3 ppb (incurred) | 1.0 ppb (incurred) | Dark | | Neg Mix | 0.3 ppb (incurred) | 1.0 ppb (incurred) | Dark |
| | 1027 | 531 | 365 | 879 | | 758 | 408 | 310 | 912 |
| | 896 | 550 | 304 | 882 | | 809 | 463 | 327 | 860 |
| | 1012 | 593 | 319 | 772 | | 778 | 520 | 293 | 763 |
| Avg = | 978 | 558 | 329 | 844 | Avg = | 782 | 464 | 310 | 845 |
| CV = | 7.3% | 5.7% | 9.7% | 7.4% | CV = | 3.3% | 12.1% | 5.5% | 8.9% |
| B/Bo = | | 0.57 | 0.34 | 0.86 | B/Bo = | | 0.59 | 0.40 | 1.08 |

The above table 6 compares results from a negative control honey with results from naturally incurred honey diluted to concentrations of 0.3 ppb and 1.0 ppb FZD/AOZ and results from known negative dark honey. Both the 0.3 ppb and 1.0 ppb samples are positive with the 1.0 ppb sample showing a stronger positive result than the 0.3 ppb sample. Both the negative control and the known negative dark honey were negative. Thus, interferences that may have been present in the dark honey were reduced or eliminated by the use of the MACRO-PREP resin.

The invention claimed is:

1. A nitrofuran metabolite compound of the formula

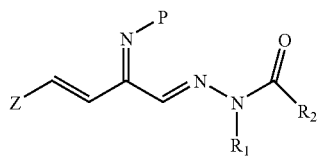

wherein P is selected from the group consisting of a bifunctional cross-linker alone, a bifunctional cross-linker conjugated further to a protein carrier, a peptide conjugated to a protein carrier, a protein, a nucleic acid, a polysaccharide, or a combination thereof;

wherein $R_1$ is either H or part of a heterocyclic ring structure said ring structure including $R_2$;

wherein $R_2$ is selected from the group consisting of NH, O when part of the heterocyclic ring structure or $NH_2$ when not part of the heterocyclic ring structure; and wherein Z is selected from the group consisting essentially of —CN, —OH, —O—CO2H, halides, carboxylate, —OR where R is an alkyl or acyl group of a low carbon chain of 11 carbons or fewer and —NHR where R is an alkyl or acyl group of a low carbon chain of 11 carbons or fewer.

2. The nitrofuran metabolite compound of claim 1 wherein $R_1$ is part of a heterocyclic ring structure of either a substituted two-carbon chain or an unsubstituted two-carbon chain and wherein when $R_1$ is part of said substituted two-carbon chain said substitution is selected from the group consisting of: (i) an oxo (═O); (ii) a 4-morpholinomethyl; (iii) a 5 membered heterocyclicalkyl ring substitution; and (iv) a 6 membered heterocyclicalkyl ring substitution.

3. The nitrofuran metabolite compound of claim 1 comprising the formula

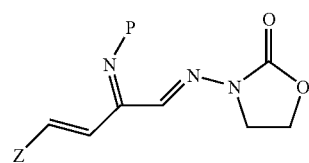

wherein P is selected from the group consisting of a bifunctional cross-linker alone, a bifunctional cross-linker conjugated further to a protein carrier, a peptide conjugated to a protein carrier, and a protein, a nucleic acid, a polysaccharide, or a combination thereof; and wherein Z is selected from the group consisting essentially of —CN, —OH, —O—CO2H, halides, carboxylate, —OR where R is an alkyl or acyl group of a low carbon chain of 11 carbons or fewer and —NHR where R is an alkyl or acyl group of a low carbon chain of 11 carbons or fewer.

4. The compound of claim 3 comprising the formula

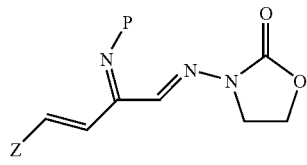

wherein P is a protein; and wherein Z is a CN group.

5. The compound of claim 4 wherein P is a thyroglobulin.

* * * * *